United States Patent
Szijarto et al.

(10) Patent No.: US 11,466,074 B2
(45) Date of Patent: Oct. 11, 2022

(54) ANTIBODIES TARGETING A GALACTAN-BASED O-ANTIGEN OF K. PNEUMONIAE

(71) Applicant: X4 PHARMACEUTICALS (AUSTRIA) GMBH, Vienna (AT)

(72) Inventors: Valeria Szijarto, Vienna (AT); Gábor Nagy, Sopron (HU); Luis Guachalla, Vienna (AT); Zehra Visram, Vienna (AT); Eszter Nagy, Vienna (AT); Jolanta Katarzyna Lukasiewicz, Wroclaw (PL)

(73) Assignee: X4 PHARMACEUTICALS (AUSTRIA) GMBH, Vienna (AT)

( * ) Notice: Subject to any disclaimer, the term of this patent is extended or adjusted under 35 U.S.C. 154(b) by 0 days.

(21) Appl. No.: 15/551,813

(22) PCT Filed: Nov. 3, 2015

(86) PCT No.: PCT/EP2015/075583
§ 371 (c)(1),
(2) Date: Aug. 17, 2017

(87) PCT Pub. No.: WO2016/131503
PCT Pub. Date: Aug. 25, 2016

(65) Prior Publication Data
US 2018/0066041 A1 Mar. 8, 2018

(30) Foreign Application Priority Data
Feb. 17, 2015 (EP) .................................... 15155448

(51) Int. Cl.
*C07K 16/12* (2006.01)
*A61K 39/00* (2006.01)
*G01N 33/569* (2006.01)

(52) U.S. Cl.
CPC ... *C07K 16/1228* (2013.01); *G01N 33/56916* (2013.01); *A61K 2039/505* (2013.01); *C07K 2317/76* (2013.01); *C07K 2317/92* (2013.01); *G01N 2333/26* (2013.01); *G01N 2800/26* (2013.01)

(58) Field of Classification Search
CPC .............. A61K 2039/505; A61K 39/40; C07K 16/1228; C07K 2317/20; C07K 2317/24; C07K 2317/76; C07K 2317/92; G01N 2333/26; G01N 2800/26; G01N 33/56916
See application file for complete search history.

(56) References Cited

U.S. PATENT DOCUMENTS 6,331,415 B1  12/2001  Cabilly et al.
2002/0177170 A1  11/2002  Luo et al.

FOREIGN PATENT DOCUMENTS

| EA | 013564 | 6/2010 |
|---|---|---|
| WO | 2003/074679 | 9/2003 |
| WO | 2009/036379 | 3/2009 |
| WO | 2010/105256 | 9/2010 |
| WO | 2012/009568 | 1/2012 |

OTHER PUBLICATIONS

Lederman et al. Mol. Immunol. 28: 1171-1181, 1991.*
Kussie et al. J. Immunol. 152:146-152, 1994.*
Li et al. PNAS 77: 3211-3214, 1980.*
Skolnick et al. Trends in Biotechnology 18: 34-39, 2000.*
Rudikoff et al. PNAS USA, 79:1979-1983, 1982.*
Vajdos et al. J. Mol. Biol. 2002, Jul. 5, 320:415-28, 2002.*
Allison, G.E. et al., "Serotype-converting bacteriophages and O-antigen modification in Shigella flexneri", Trends Microbiol Jan. 2000;8(1):17-23.
Brodeur, B.R. et al., "Mouse-Human Myeloma Partners for the Production of Heterohybridomas" 1987, Monoclonal Antibody Production Techniques and Applications, (Marcel Dekker, Inc., New York), pp. 51-63.
Clarke, B.R. et al., "Molecular Cloning of the rfb Region of Klebsiella pneumoniae Serotype O1:K20: the rfb Gene Cluster Is Responsible for Synthesis of the D-Galactan I O Polysaccharide", J Bacteriol Jul. 1992;174(14):4614-21.
Hansen, D.S. et al., "Klebsiella pneumoniae Lipopolysaccharide O Typing: Revision of Prototype Strains and O-Group Distribution among Clinical Isolates from Different Sources and Countries" J Clin Microbiol Jan. 1999;37(1):56-62.
Hsieh, P. et al., D-galactan II is an immunodominant antigen in O1 lipopolysaccharide and affects virulence in Klebsiella pneumoniae: implication in vaccine design Front Microbiol 2014; vol. 5:608, pp. 1-14.

(Continued)

*Primary Examiner* — Sarvamangala Devi
(74) *Attorney, Agent, or Firm* — Wenderoth, Lind & Ponack, L.L.P.

(57) ABSTRACT

The invention provides for an isolated antibody that specifically recognizes a galactan-III epitope of the lipopolysaccharide (LPS) O-antigen structure of *Klebsiella pneumoniae*, which epitope is incorporated in galactan-III repeating units, wherein the galactan-III repeating unit is a branched galactose homopolymer of Formula (I). The invention further provides for a pharmaceutical or diagnostic preparation comprising said antibody, and a method of producing said antibody.

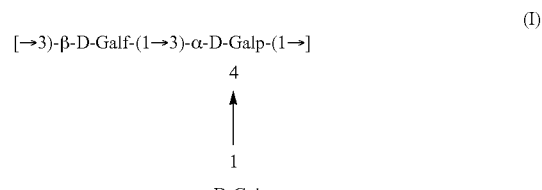

Figures 3, 4:
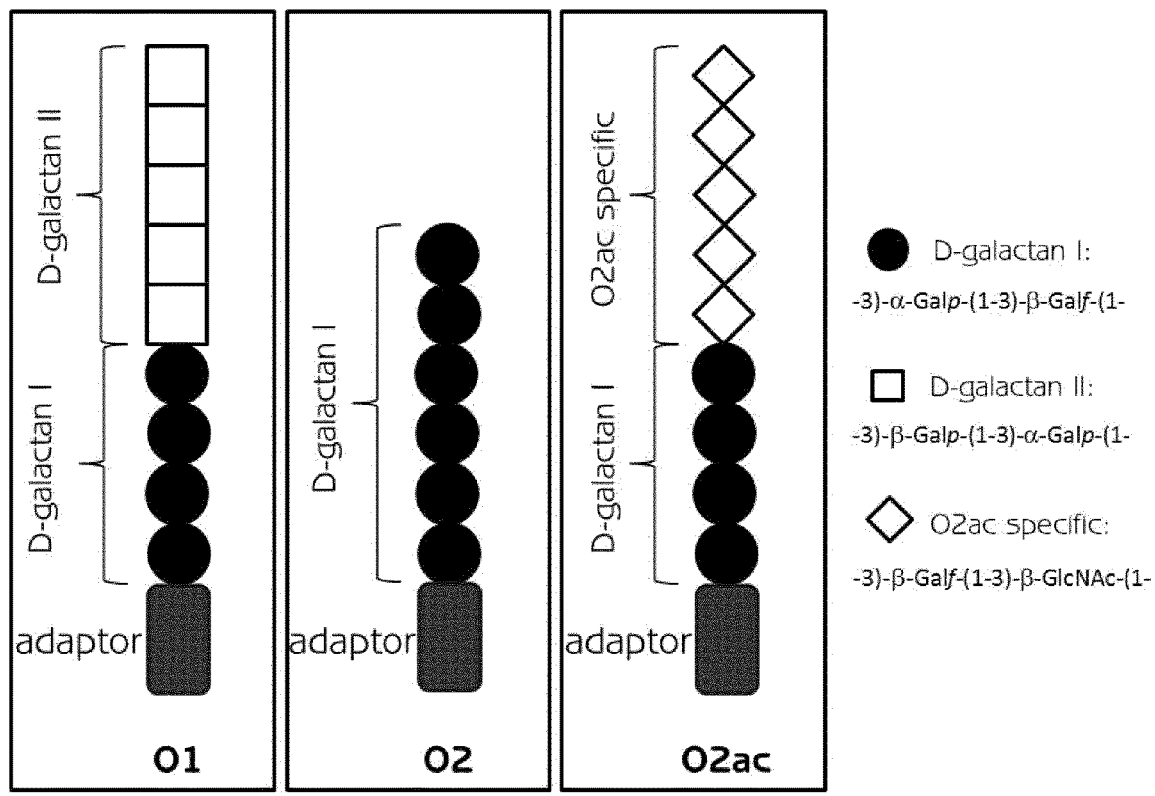

14 Claims, 11 Drawing Sheets
Specification includes a Sequence Listing.

(56) References Cited

OTHER PUBLICATIONS

Kelly, R.F. et al., "Structures of the O-antigens of Klebsiella serotypes 02 (2a,2e), 02 (2a,2e,2h), and 02 (2a,2f,2g), members of a family of related D-galactan O-antigens in Klebsiella spp" Journal of Endotoxin Research 1995;2:131-40.
Kohler, G. et al., "Continuous cultures of fused cells secreting antibody of predefined specificity" 1975, Nature 256:495-497.
Kozbor, D. et al., "A Human Hybrid Myeloma for Production of Human Monoclonal Antibodies" 1984, J. 30 Immunol. 133:3001-3005.
Lee, M. et al., "Expression and functional reconstitution of a recombinant antibody (Fab') specific for human apolipoprotein B-100" 2003, J. Biotechnology 101:189-198.
Lefranc, M. et al., "IMGT, the international ImMunoGeneTics database" 1999, Nucleic Acids Res. 27: 209-212.
Prassler, J. et al., "In vitro affinity maturation of HuCAL antibodies: complementarity determining region exchange and RapMAT technology" 2009, Immunotherapy, vol. 1(4), pp. 571-583.
Sheedy, C. et al., "Isolation and affinity maturation of hapten-specific antibodies" 2007, Biotechnol. Adv., vol. 25(4), pp. 333-352.
Trautmann, M. et al., O-Antigen Seroepidemiology of Klebsiella Clinical Isolates and Implications for Immunoprophylaxis of Klebsiella Infections Clin Diagn Lab Immunol Sep. 1997;4(5):550-555.
Umana, P. et al., "Engineered glycoforms of an antineuro-blastoma IgG1 with optimized antibody-dependent cellular cytotoxic activity" 1999, Nature Biotech. 17:176-180.
Wibbenmeyer, J. et al., "Cloning, expression, and characterization of the Fab fragment of the anti-lysozyme antibody HyHEL-5" 1999, Biochim Biophys Acta 1430(2):191-202.

Extended European Search Report dated May 26, 2015, from European Application No. 15155448.2, 5 pages.
International Search Report dated Jan. 13, 2016, from International Application No. PCT/EP2015/075583, 3 pages.
Written Opinion dated Jan. 13, 2016, from International Application No. PCT/EP2015/075583, 6 pages.
Office Action dated Jun. 11, 2019 in Russian Patent Application No. 2017132168, with English Translation.
Ladner R.C., "Mapping the Epitopes of Antibodies", Biotechnology and Genetic Engineering Reviews, 2007, vol. 24, No. 1, pp. 1-30.
Vinogradov et al., "Structures of Lipopolysaccharides from Klebsiella pneumoniae", Journal of Biological Chemistry, 2002, vol. 277, No. 28, pp. 25070-25081.
Communication pursuant to Article 94(3) EPC dated Jul. 20, 2020 in corresponding European Patent Application No. 15790526.6.
Du et al., "Molecular Basis of Recognition of Human Osteopontin by 23C3, a Potential Therapeutic Antibody for Treatment of Rheumatoid Arthritis", Journal of Molecular Biology, 2008, vol. 382, No. 4, pp. 835-842.
Caldas et al., "Humanization of the anti-CD18 antibody 6.7: an unexpected effect of a framework residue in binding to antigen", Molecular Immunology, 2003, vol. 39, No. 15, pp. 941-952.
Kunik et al., "Structural Consensus among Antibodies Defines the Antigen Binding Site", PLoS Computational Biology, 2012, vol. 8, No. 2, p. e1 002388, 12 pages.
Casadevall et al., "Immunoglobulin isotype influences affinity and specificity", Proceedings of the National Academy of Sciences, 2012, vol. 109, No. 31, pp. 12272-12273.
Office Action dated Aug. 5, 2020 in corresponding Chinese Patent Application No. 201580075698.6, with partial English translation.

\* cited by examiner

Fig. 1

Table 1: CDR sequences using KABAT nomenclature

Heavy Chain Variable Region (VH)

| SEQ ID | mAb Name | SEQ ID CDR1 | VH CDR1 | SEQ ID CDR2 | VH CDR2 | SEQ ID CDR3 | VH CDR3 |
|---|---|---|---|---|---|---|---|
| 21 | 8E3-E5 | 1 | FTFSNYWIN | 2 | EIRLKSNNYATYYESVKG | 3 | TRHVGGFAN |
| 23 | 9H9-H7 | 4 | LAFSNYWMN | 5 | EIRLKSNSYSTHYAESVKG | 6 | TPERGGFPY |
| 25 | 5A4-A7 | 7 | FTFSDYWMN | 8 | EIRLKSNNFATYYAESVKG | 9 | LPERGGFFY |
| 27 | 2D8-A10 | 10 | FTFSNYWMN | 11 | EIRLKSNNYATHYAESVKG | 12 | TPERGGFFY |

Light Chain Variable Region (VL)

| SEQ ID | mAb Name | SEQ ID VL CDR4 | VL CDR4 | SEQ ID VL CDR5 | VL CDR5 | SEQ ID VL CDR6 | VL CDR6 |
|---|---|---|---|---|---|---|---|
| 22 | 8E3-E5 | 13 | RSSQSLIYSSNQKNCLA | 14 | WASTRES | 15 | HQYLSSYT |
| 24 | 9H9-H7 | 16 | RSSQSIVHSDGSTYLH | 17 | KVSNRFS | 18 | SQSTHVPWT |
| 26 | 5A4-A7 | 19 | RSSQSIVHSDGNTYLH | 20 | LVSNRFS | 18 | SQSTHVPWT |
| 28 | 2D8-A10 | 19 | RSSQSIVHSDGNTYLH | 17 | KVSNRFS | 18 | SQSTHVPWT |

Fig. 2

8E3-E5

8E3-E5: VH: SEQ ID 21

EVKLQESGGGLVQPGGSMKLSCVASGFTFSNYWINWVRQSPEKGLEWVAEIRLKSNNYATYYVESVKGRFTISRDD
SKSSVYLQMNNLRAEDTGIYYCTKEYGGFANWGQGTTVTVSS

8E3-E5: VL: SEQ ID 22

NIMMTQSPSSLAVSAGEKVTMSCKSSQSLLYSSNQKNCLAWYQRKPGQSPKLLISWASTRESGVPDRFTGSGSGTD
FTLTISSVQAEDLAVYYCHQYLSSYTFGGGTKLEIK

9H9-H7

9H9-H7: VH: SEQ ID 23

EVKLQESGGGLVQPGGSMKLSCVASGLAFSNYWMNWVRQSPEKGLEWVAEIRLKSNSYSTHYAESVKGRFTISRDD
SKSGVYLQMNNLRAEDTGIYYCTPEFGGFPYWGQGTTVTVSS

9H9-H7: VL: SEQ ID 24

DVVMTQTPLSLPVSLGDHASISCRSSQSLVHSDGSTYLHWYLQKPGQSPKLLIYKVSNRFSGVPDRFSGSGSGTDF
TLKISRVEAEDLGVYFCSQSTHVPWTFGGGTKLEIK

5A4-A7

5A4-A7: VH: SEQ ID 25

EVNLEESGGGLVQPGGSMKLSCVASGFTFSDYWMNWVRQSPEKGLEWVAEIRLKSNNYATYYAESVKGRFTISRDD
SKRSVYLRVNNLRVEDTGIYYCLPEFGGFFYWGQGTLVTVSA

5A4-A7: VL: SEQ ID 26

DVLMTQTPLSLPVRLGDQASISCRSSQSLVHSDGNTYLHWYLQRPGQSPKLLINLVSNRFSGVPDRFSGSGSGTDF
TLKISRVEAEDLGVYFCSQSTHVPWTFGGGTKLEIK

2D8-A10

2D8-A10: VH: SEQ ID 27

EVKLQESGGGLVQPGGSMKLSCVVSGFTFSNYWMNWVRQSPEKGLEWVAEIRLKSNNYATHYAESVKGRFTISRDD
SKSSVYLQMNNLRAEDTGIYYCTPEFGGFFYWGQGTTVTVSS

2D8-A10: VL: SEQ ID 28

DVVMTQTPLSLPVNLGDQASISCRSSQSLVHSDGNTYLHWYLQKPGQSPKLLIYKVSNRFSGVPDRFSGSGSGTDF
TLKISRVEAEDLGVYFCSQSTHVPWTFGGGTKLEIK

Fig. 2 continued

G3-43

G3-43 VH: (including CDR sequences of VH 5A4-A7) SEQ ID 29
EVQLLESGGGLVQPGGSLRLSCAASGFTFSDYWMNWVRQAPGKGLEWVAEIRLKSNNYATYYAESVKGRFTISRDN
SKNTVYLQMNSLRAEDTAVYYCLPEFGGFFYWGQGTLVTVSS G3-43 VL: (including CDR sequences of VL 5A4-A7) SEQ ID 30
DVVMTQSPLSLPVTPGEPASISCRSSQSLVHSDGNTYLHWYLQKPGQSPQLLINLVSNRFSGVPDRFSGSGSGTDF
TLKISRVEAEDVGVYYCSQSTHVPWTFGGGTKVEIK

G3-46

G3-46 VH: (including CDR sequences of VH 5A4-A7) SEQ ID 31
EVQLLESGGGLVQPGGSLRLSCAASGFTFSDYWMNWVRQAPGKGLEWVAEIRLKSNNYATYYAESVKGRFTISRDD
SKRTVYLQMNSLRAEDTAVYYCLPEFGGFFYWGQGTLVTVSS G3-46 VL: (including CDR sequences of VL 5A4-A7) SEQ ID 32
DVVMTQSPLSLPVTPGEPASISCRSSQSLVHSDGNTYLHWYLQKPGQSPQLLINLVSNRFSGVPDRFSGSGSGTDF
TLKISRVEAEDVGVYYCSQSTHVPWTFGGGTKVEIK

G3-77

G3-77 VH: (including CDR sequences of VH 9H9-H7) SEQ ID 33
EVQLLESGGGLVQPGGSLRLSCAASGLAFSNYWMNWVRQAPGKGLEWVAEIRLKSNSYSTHYAESVKGRFTISRDD
SKSTVYLQMNSLRAEDTAVYYCTPEFGGFPYWGQGTLVTVSS G3-77 VL: (including CDR sequences of VL 5A4-A7) SEQ ID 34
DVVMTQSPLSLPVTPGEPASISCRSSQSLVHSDGNTYLHWYLQKPGQSPQLLINLVSNRFSGVPDRFSGSGSGTDF
TLKISRVEAEDVGVYYCSQSTHVPWTFGGGTKVEIK

G3-78

G3-78 VH: (including CDR sequences of VH 9H9-H7) SEQ ID 35
EVQLLESGGGLVQPGGSLRLSCAASGLAFSNYWMNWVRQAPGKGLEWVAEIRLKSNSYSTHYAESVKGRFTISRDD
SKSTVYLQMNSLRAEDTAVYYCTPEFGGFPYWGQGTLVTVSS G3-78 VL: (including CDR sequences of VL 5A4-A7) SEQ ID 36
DVQMTQSPSSLSASVGDRVTITCRSSQSLVHSDGNTYLHWYQQKPGKSPKLLINLVSNRFSGVPSRFSGSGSGTDF
TLTISSLQPEDFATYYCSQSTHVPWTFGGGTKVEIK

G3-97

G3-97 VH: (including CDR sequences of VH 2D8-A10) SEQ ID 37
EVQLLESGGGLVQPGGSLRLSCAVSGFTFSNYWMNWVRQAPGKGLEWVAEIRLKSNNYATHYAESVKGRFTISRDD
SKSTVYLQMNSLRAEDTAVYYCTPEFGGFFYWGQGTLVTVSS G3-97 VL: (including CDR sequences of VL 5A4-A7) SEQ ID 38
DVVMTQSPLSLPVTPGEPASISCRSSQSLVHSDGNTYLHWYLQKPGQSPQLLINLVSNRFSGVPDRFSGSGSGTDF
TLKISRVEAEDVGVYYCSQSTHVPWTFGGGTKVEIK

A)

| Sequenced strains | uge-his distance (bp) |
|---|---|
| HS11286 | 9218 |
| KCTC 2242 | 12057 |
| 1084 | 12053 |
| NTUH-K2044 01 | 12056 |

| 1 | #063 | O1 |
| 2 | #074 | O1 |
| 3 | #080 | O1 |
| 4 | #081 | O1 |
| 5 | #079 | O2 |
| 6 | #098 | O2ac |
| 7 | #193 | O1 |

| | strain | O-type | gtr |
|---|---|---|---|
| 1 | #63 | O1 | - |
| 2 | #79 | O2 | + |
| 3 | Kp5 | O2 | - |
| 4 | Kp55 | O2 | - |
| 5 | Kp117 | O2 | - |
| 6 | Kp19 | O2 | + |
| 7 | Kp30 | O2 | + |
| 8 | Kp67 | O2 | + |
| 9 | Kp3 | O1 | - |
| 10 | Kp69 | O1 | - |
| 11 | Kp111 | O1 | - |
| 12 | Kp24 | O1 | + |
| 13 | Kp36 | O1 | + |
| 14 | Kp97 | O1 | + |

| | LPS sample | Reactivity with gal-III specific serum |
|---|---|---|
| 1 | O2 gtr+ | + |
| 2 | O2 gtr- | - |
| 3 | O2 gtr- / uninduced empty vector | - |
| 4 | O2 gtr- / induced empty vector | - |
| 5 | O2 gtr- / gtr plasmid uninduced | + |
| 6 | O2 gtr- / gtr plasmid induced | + |

Fig. 9

| mAb | VH | VL | Fluorescence intensity (FL-1) |
|---|---|---|---|
| 5A4 Chimeric | 5A4-A7 | 5A4-A7 | 38918 |
| G3-40 | 5A4-A7 | 5A4-A7 | 17108 |
| G3-41 | 5A4-A7 | 5A4-A7 | 19965 |
| G3-42 | 5A4-A7 | 5A4-A7 | 22187 |
| G3-43 | 5A4-A7 | 5A4-A7 | 22801 |
| G3-44 | 5A4-A7 | 5A4-A7 | 27903 |
| G3-45 | 5A4-A7 | 5A4-A7 | 29942 |
| G3-46 | 5A4-A7 | 5A4-A7 | 35252 |
| G3-49 | 5A4-A7 | 2D8-A10 | 27470 |
| G3-51 | 5A4-A7 | 9H9-H7 | 17701 |
| G3-52 | 5A4-A7 | 9H9-H7 | 20058 |
| G3-53 | 5A4-A7 | 2D8-A10 | 21597 |
| G3-54 | 5A4-A7 | 2D8-A10 | 22973 |
| G3-55 | 5A4-A7 | 2D8-A10 | 29562 |
| 2D8 Chimeric | 2D8-A10 | 2D8-A10 | 22436 |
| G3-85 | 2D8-A10 | 2D8-A10 | 24789 |
| G3-86 | 2D8-A10 | 2D8-A10 | 28199 |
| G3-87 | 2D8-A10 | 2D8-A10 | 23433 |
| G3-88 | 2D8-A10 | 2D8-A10 | 35420 |
| G3-89 | 2D8-A10 | 2D8-A10 | 18449 |
| G3-90 | 2D8-A10 | 2D8-A10 | 17514 |
| G3-91 | 2D8-A10 | 2D8-A10 | 19934 |
| G3-92 | 2D8-A10 | 2D8-A10 | 23634 |
| G3-93 | 2D8-A10 | 2D8-A10 | 23929 |
| G3-95 | 2D8-A10 | 5A4-A7 | 30144 |
| G3-96 | 2D8-A10 | 9H9-H7 | 28988 |
| G3-97 | 2D8-A10 | 5A4-A7 | 35792 |
| G3-98 | 2D8-A10 | 9H9-H7 | 16983 |

| mAb | VH | VL | Fluorescence intensity (FL-1) |
|---|---|---|---|
| 9H9 Chimeric | 9H9-H7 | 9H9-H7 | 30067 |
| G3-57 | 9H9-H7 | 9H9-H7 | 30397 |
| G3-59 | 9H9-H7 | 9H9-H7 | 23804 |
| G3-61 | 9H9-H7 | 9H9-H7 | 18207 |
| G3-62 | 9H9-H7 | 9H9-H7 | 20349 |
| G3-63 | 9H9-H7 | 9H9-H7 | 22465 |
| G3-64 | 9H9-H7 | 9H9-H7 | 23186 |
| G3-66 | 9H9-H7 | 9H9-H7 | 28715 |
| G3-67 | 9H9-H7 | 9H9-H7 | 29945 |
| G3-68 | 9H9-H7 | 9H9-H7 | 30977 |
| G3-70 | 9H9-H7 | 2D8-A10 | 20252 |
| G3-71 | 9H9-H7 | 2D8-A10 | 17153 |
| G3-73 | 9H9-H7 | 2D8-A10 | 20246 |
| G3-74 | 9H9-H7 | 2D8-A10 | 22200 |
| G3-75 | 9H9-H7 | 2D8-A10 | 23805 |
| G3-76 | 9H9-H7 | 5A4-A7 | 28495 |
| G3-77 | 9H9-H7 | 5A4-A7 | 27983 |
| G3-78 | 9H9-H7 | 5A4-A7 | 37587 |
| G3-79 | 9H9-H7 | 2D8-A10 | 17647 |
| G3-80 | 9H9-H7 | 2D8-A10 | 17238 |
| G3-81 | 9H9-H7 | 2D8-A10 | 19754 |
| Negative ctrl mAb#1 | - | - | 176 |
| Negative ctrl mAb#2 | - | - | 277 |
| Secondary mAb only | - | - | 428 |

Fig. 10.
A)
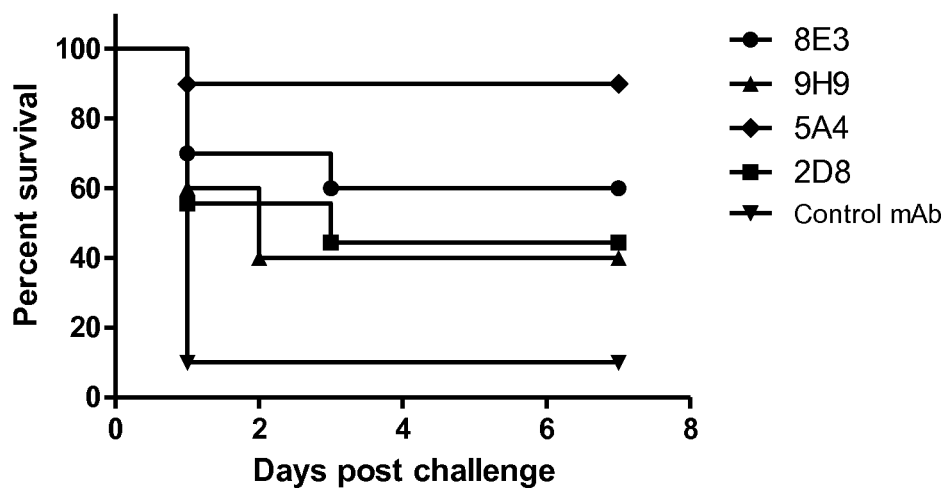
B)
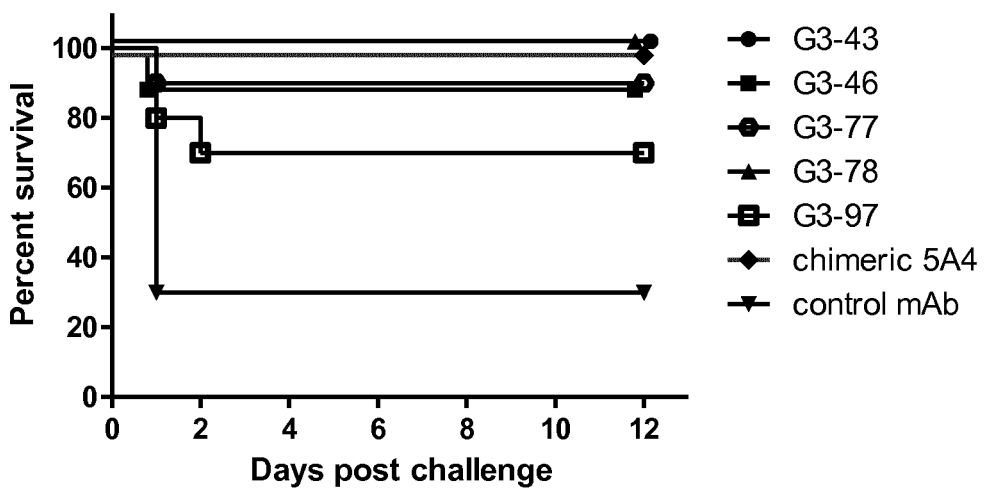

Fig. 12

ANTIBODIES TARGETING A GALACTAN-BASED O-ANTIGEN OF K. PNEUMONIAE

FIELD OF THE INVENTION

The invention refers to a monoclonal antibody that specifically recognizes a unique galactan-based O-antigen structure, which is associated with the majority of epidemic multi-drug resistant *Klebsiella pneumoniae* ST258.

BACKGROUND OF THE INVENTION

*Klebsiella pneumoniae* is an important enterobacterial pathogen responsible for urinary tract infections, pneumonia, and septicaemia that cause significant morbidity and mortality. Multi-drug resistant (MDR) strains have recently emerged and spread globally, against which therapeutic options are limited.

Lipopolysaccharide (LPS) is the major constituent of the outer leaflet of the outer membrane of Gram-negative bacteria, such as *Klebsiella pneumoniae*. LPS has three major structurally and functionally diverse parts: i) lipid A, which is also known as endotoxin, ii) core-oligosaccharide, and iii) O-antigen, which is built up of repeating units of oligosaccharide blocks.

*K. pneumoniae* O-antigens are surface antigens of diverse structure, defining different O-types. The most common serotypes among the currently recognized 7 O-types appear to be O1 and O2, which together were reported to be expressed by the majority (i.e. >50%) of all isolates(1;2). Both O1 and O2 antigens are composed of galactose polymers, i.e. galactans. The O2 antigen (also known as O2a or O2ab in order to differentiate from O2ac described below) is made up of repeats of the so-called galactan-I disaccharide (see FIG. 3). In contrast, the O1 and O2ac antigens do contain additional distinct structures besides galactan-I as follows: the LPS core-proximal portion is constituted of repeats of galactan-I, which is capped by either galactan-II (a different homopolymer of galactose in case of O1) or a non-galactan repeating unit (in case of O2ac).

The serotypes sharing the galactan-I O-subunit carry a highly similar rfb locus encoding synthesis and export of this structure. The nucleotide sequence of the galactan-I encoding operon has been partially determined (3). The locus was described to be 7.3 kb long comprising 6 genes. Complementation of rough mutants of *K. pneumoniae* O1, *E. coli* K-12 or *Salmonella enterica* serovar Typhimurium by the cloned rfb locus restored production of smooth LPS consisting of galactan-I O-antigen repeats. This suggests that these 6 genes are essential and sufficient for the production of galactan-I O-antigen side chains (3). Structural modification of D-galactan-I in different O2 *Klebsiella* strains was published by Kelly et al. (5). Nevertheless, the genetic background for these modifications remains to be elucidated. The genetic determinants encoding galactan-II repeating units (i.e. those capping either galactan-I or galactan-III presented herewith) were recently described (4). Importantly, these genes are unrelated to the genetic determinants responsible for the conversion of galactan-I units to galactan-III. Consequently, O1 serotype strains, besides expressing the serotype determining surface located galactan-II repeating units can express either galactan-I or galactan-III repeating units bridging the Lipid A-core and galactan-II repeats.

Multi-drug resistant (MDR) strains of *K. pneumoniae* that have emerged recently cause a significant proportion of *K. pneumoniae* infections. Treatment options against MDR strains are getting very limited as they have evolved resistance to most classes of clinically relevant antibiotics. Therefore, alternative treatment options, e.g. passive immunization with monoclonal antibodies (mAbs) hold a great promise for the future.

There is a need for new targets of *Klebsiella pneumoniae*. In particular, targets need to be identified which are immunorelevant and may be used for developing therapies and diagnostics.

SUMMARY OF THE INVENTION

It is the objective of the present invention to provide for an antibody directed against *K. pneumoniae*, in particular MDR strains, with improved relevance to target the pathogen, to be used for the prevention or therapy of *K. pneumoniae* infections. It is further the objective to provide means and methods that are capable of diagnosing *K. pneumoniae* bacteria, such as MDR strains, in a rapid and reliable manner.

The object is solved by the subject of the present invention.

According to the invention there is provided an isolated antibody that specifically recognizes a galactan-III (gal-III) epitope of the lipopolysaccharide (LPS) O-antigen structure of *Klebsiella pneumoniae*, which epitope is incorporated in galactan-III repeating units, wherein the galactan-III repeating unit is a branched galactose homopolymer of Formula (I)

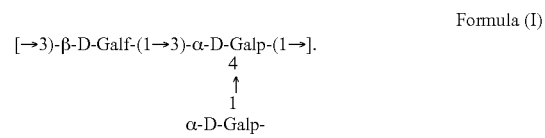

Formula (I)

Specifically the galactan-III epitope is incorporated in an O-antigen structure comprising at least 2 gal-III repeating units, or at least 3, 4, or 5.

According to a specific aspect, the antibody preferentially binds to the galactan-III epitope relative to the galactan-I epitope, or which does not cross-react with the galactan-I epitope, wherein the galactan-I (gal-I) epitope is incorporated in galactan-I repeating units of the LPS O2a-antigen structure of *Klebsiella pneumoniae*, and wherein the galactan-I repeating unit is a linear galactose homopolymer of Formula (II)

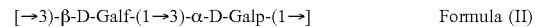 Formula (II)

For example, the antibody of the invention is a gal-III specific antibody which is specifically recognizing or binding the O-antigen structure comprising the gal-III antigen. Exemplary antibodies are listed in FIGS. 1 and 2, or variants of such antibodies. For the purpose of providing variants, the antibodies are herein referred to as parent antibodies, and CDR or framework sequences are herein referred to as parent CDR or parent framework sequences.

According to a specific aspect, the antibody comprises recombinant CDR and framework sequences, e.g. of different origin, wherein at least one of the CDR and framework sequences includes human, humanized, chimeric, murine or affinity matured sequences, preferably wherein the framework sequences are of any immunoglobulin isotype, and in particular of an IgG antibody.

Specifically, the antibody of the invention is cross-specific to bind the gal-III and gal-I epitopes, and preferentially binds to the gal-III antigenic structure relative to a gal-I antigenic structure of an O2 antigen of *K. pneumoniae*, e.g. with an affinity which is higher to bind the gal-III as compared to the gal-I antigen. According to a specific embodiment, the antibody has at least two-fold greater affinity for binding the gal-III antigen as compared to the gal-I antigen, specifically with at least two-fold difference, or at least three-fold, at least four-fold, at least 5-fold, or even at least 10-fold difference, e.g. difference in affinity and/or avidity. For example, the Kd difference to preferentially bind the gal-III antigen over the gal-I antigen is at least 0.5 or 1 log, or even at least 2 logs, or at least 3 logs different, as determined by an immunoassay, preferably immunoblotting, ELISA or other immunological methods.

The antibody of the invention is specifically further characterized that it does not cross-react with any other *K. pneumoniae* antigen, and/or the antibody binds to any other *K. pneumoniae* antigen with a lower affinity, e.g. where the Kd difference to preferentially bind the gal-III antigen over other *K. pneumoniae* antigens (other than the gal-III or gal-I antigens) is at least 2 logs, preferably at least 3 logs.

Specifically, the functionally active variant is a functionally active CDR variant which comprises at least one point mutation in the parent CDR sequence, and comprises or consists of the amino acid sequence that has at least 60% sequence identity with the parent CDR sequence, preferably at least 70%, at least 80%, at least 90% sequence identity.

A specific variant is e.g., a humanized variant of the parent antibody, wherein the parent CDR sequences are incorporated into human or humanized framework sequences, wherein optionally 1, 2, 3, or 4 amino acid residues of each of the parent CDR sequences may be further mutated by introducing point mutations to improve the stability, specificity and affinity of the parent or humanized antibody.

Specifically, the VH or heavy chain (HC) sequences of such variants may be substituted by VH and HC sequences of another variant, respectively, in particular where the other variant is any other variant of the same parent antibody.

Specifically, the VL or light chain (LC) sequences of such variants may be substituted by VL and LC sequences of another variant, respectively, in particular where the other variant is any other variant of the same parent antibody.

Specifically, the galactan-III epitope is expressed by multi-drug resistant (MDR) *Klebsiella pneumoniae*, more specifically the MDR clone ST258. Specifically, the galactan-III epitope is of the multi-drug resistant (MDR) *Klebsiella pneumoniae*.

According to a specific embodiment, the antibody has an affinity to bind the galactan-III epitope with a Kd of less than $10^{-7}$M, preferably less than $10^{-8}$M, even more preferably less than $10^{-9}$M.

Variants of parent antibodies which are produced by affinity maturation, herein referred to as affinity-matured variants, may have an increased binding affinity, with a Kd difference of at least 1 log, or 2 logs, or 3 logs, as compared to the parent antibody. Affinity matured variants typically have an affinity to bind the gal-III antigen with a Kd of less than $10^{-8}$M, or less than $10^{-9}$M. If the parent antibody has an affinity with a Kd of less than $10^{-8}$M, or less than $10^{-9}$M, and the parent antibody is undergoing affinity maturation, the affinity matured variant may have an even higher affinity with a Kd of less than $10^{-9}$M and less than $10^{-10}$M, respectively.

According to a specific aspect, the antibody is a neutralizing antibody. Specifically the antibody is neutralizing endotoxin (i.e. LPS) of *Klebsiella pneumoniae* strains expressing the galactan-III epitope, as determined by an in vitro or in vivo detection method. Specifically, the antibody neutralizes endotoxic effect of specific LPS molecules in vitro.

Specifically, the antibody is neutralizing endotoxin of *Klebsiella pneumoniae* strains expressing the galactan-III epitope, wherein the neutralization potency is at least the potency of a reference antibody (e.g. the reference antibody 2D8-A10), which comprises a) a CDR1 consisting of the amino acid sequence of SEQ ID 10; and
b) a CDR2 consisting of the amino acid sequence of SEQ ID 11; and
c) a CDR3 consisting of the amino acid sequence of SEQ ID 12; and
d) a CDR4 consisting of the amino acid sequence of SEQ ID 19; and
e) a CDR5 consisting of the amino acid sequence of SEQ ID 17; and
f) a CDR6 consisting of the amino acid sequence of SEQ ID 18, according to the nomenclature of Kabat. Such CDR sequences are designated according to the numbering system of Kabat.

In the following, unless indicated otherwise, reference is made to the CDR sequences as numbered according to Kabat, i.e. as determined according to Kabat nomenclature (see Kabat et al., Sequences of Proteins of Immunological Interest, 5$^{th}$ Ed. Public Health Service, U.S. Department of Health and Human Services. (1991)), and in particular those CDR sequences as listed in Table 1. It is well understood that the invention and the scope of the claims shall also encompass the same antibodies and CDR, yet with a different numbering and designated CDR region, where CDR regions are defined according to the IMGT system (The international ImMunoGeneTics, Lefranc et al., 1999, Nucleic Acids Res. 27: 209-212).

Specifically, the *Klebsiella pneumoniae* strain targeted by the antibody of the invention is characterized by a rfb$_{gal-I}$ locus incorporating additional glycosyl transferase (gtr) genes.

According to a specific aspect, the antibody recognizes the MDR *Klebsiella pneumoniae* clone ST258, in particular, a strain expressing the galactan-III epitope.

A specific embodiment refers to an antibody which is any of a full-length monoclonal antibody, an antibody fragment thereof comprising at least one antibody domain incorporating the binding site, or a fusion protein comprising at least one antibody domain incorporating the binding site, specifically wherein the antibody is a non-naturally occurring antibody which comprises a randomized or artificial amino acid sequence.

Specifically, the antibody is an antibody selected from the group consisting of murine, lama, rabbit, goat, cow, chimeric, humanized or human antibodies, heavy-chain antibodies, Fab, Fd, scFv and single-domain antibodies like VH, VHH or VL, preferably a human IgG antibody or a murine IgG antibody.

Specifically, the antibody is a monoclonal antibody.

According to a specific embodiment, the antibody comprises at least an antibody heavy chain variable region or domain (VH), which is characterized by any of the CDR1 to CDR3 sequences as listed in Table 1, which are designated according to the numbering system of Kabat, or functionally active CDR variants thereof.

According to a specific aspect, the invention provides for exemplary (parent) antibodies as detailed in the figures provided herein, and further antibody variants of such parent antibodies, in particular including variants binding to essentially the same epitope, as the parent antibody which is characterized by the specific binding site formed by the VH and the VL amino acid sequences of FIG. 2, or else by the respective CDR sequences of Table 1. Such antibodies may e.g. be functionally active variant antibodies obtained by modifying the respective CDR or antibody sequence of the parent antibody. It is well understood that any antibody sequence as described herein is considered a "parent" sequence which is subject to variation, e.g. by point mutations.

The antibodies described in the examples are of murine origin or humanized forms thereof. Variants which are obtained by humanization and optionally affinity maturation may be engineered using well-known techniques. These variant antibodies bind to the target antigen, thus, are considered functionally active. It is feasible that also variant VH or VL domains, e.g. with modifications in the respective FR or CDR sequences may be used, which are functionally active, e.g. binding to the same epitope or comprising the same binding site or having the same binding characteristics as the parent antibody. It is also feasible that some of the FR or CDR sequences of the antibodies described herein may be exchanged by those of other antibodies, e.g. of antibodies as listed in Table 1.

Specifically, the antibody of the invention comprises any of the CDR sequences of the antibody heavy chain variable region as depicted in FIG. 1 (Table 1) or functionally active CDR variants thereof and/or a VH amino acid sequence selected from any of the VH sequences as depicted in FIG. 2 or functionally active variants thereof, e.g. an antibody heavy chain (HC) or VH amino acid sequence which is comprising CDR1, 2, and 3, wherein any of the CDR1 sequences 1, 4, 7, or 10; and/or any of the CDR2 sequences 2, 5, 8, or 11; and/or any of the CDR3 sequences 3, 6, 9, or 12; or comprising any of the VH sequences 19, 21, 23, or 25.

Specifically, the antibody is

A)

selected from the group consisting of group members i) to iv), wherein i)

is an antibody which comprises a) a CDR1 consisting of the amino acid sequence of SEQ ID 1; and b) a CDR2 consisting of the amino acid sequence of SEQ ID 2; and c) a CDR3 consisting of the amino acid sequence of SEQ ID 3;

ii)

is an antibody which comprises a) a CDR1 consisting of the amino acid sequence of SEQ ID 4; and b) a CDR2 consisting of the amino acid sequence of SEQ ID 5; and c) a CDR3 consisting of the amino acid sequence of SEQ ID 6;

iii)

is an antibody which comprises a) a CDR1 consisting of the amino acid sequence of SEQ ID 7; and b) a CDR2 consisting of the amino acid sequence of SEQ ID 8; and c) a CDR3 consisting of the amino acid sequence of SEQ ID 9;

iv)

is an antibody which comprises a) a CDR1 consisting of the amino acid sequence of SEQ ID 10; and b) a CDR2 consisting of the amino acid sequence of SEQ ID 11; and c) a CDR3 consisting of the amino acid sequence of SEQ ID 12;

or

B) an antibody which is a functionally active variant of a parent antibody that is any of the group members of A, which comprises at least one functionally active CDR variant of any of the CDR1, CDR2 or CDR3 of the parent antibody.

Specifically, the functionally active variant is a functionally active CDR variant which comprises at least one point mutation in the parent CDR sequence, and comprises or consists of the amino acid sequence that has at least 60% sequence identity with the parent CDR sequence, preferably at least 70%, at least 80%, at least 90% sequence identity.

Specifically, the antibody comprises a VH amino acid sequence selected from any of the VH sequences as depicted in FIG. 2.

According to a specific embodiment, the antibody further comprises an antibody light chain variable region or domain (VL), which comprises any of the CDR4 to CDR6 sequences as listed in Table 1, which are designated according to the numbering system of Kabat, or functionally active CDR variants thereof.

Specifically, the antibody of the invention comprises any of the CDR sequences of the antibody light chain variable region as depicted in FIG. 1 (Table 1) or functionally active CDR variants thereof and/or a VL amino acid sequence selected from any of the VL sequences as depicted in FIG. 2 or functionally active variants thereof, e.g. an antibody light chain (LC) or VL amino acid sequence which is comprising CDR4, 5, and 6, wherein any of the CDR4 sequences 13, 16, or 19; and/or any of the CDR5 sequences 14, 17, or 20; and/or any of the CDR6 sequences 3, 6, 9, or 12; or comprising any of the VH sequences 15 or 18, or comprising any of the VL sequences 20, 22, 24, or 26.

Specifically, the antibody is

A)

selected from the group consisting of group members i) to iv), wherein i)

is an antibody which comprises a) a CDR4 consisting of the amino acid sequence of SEQ ID 13; and b) a CDR5 consisting of the amino acid sequence of SEQ ID 14; and c) a CDR6 consisting of the amino acid sequence of SEQ ID 15;

ii)

is an antibody which comprises a) a CDR4 consisting of the amino acid sequence of SEQ ID 16; and b) a CDR5 consisting of the amino acid sequence of SEQ ID 17; and c) a CDR6 consisting of the amino acid sequence of SEQ ID 18;

iii)

is an antibody which comprises a) a CDR4 consisting of the amino acid sequence of SEQ ID 19; and b) a CDR5 consisting of the amino acid sequence of SEQ ID 20; and c) a CDR6 consisting of the amino acid sequence of SEQ ID 18;
iv)
is an antibody which comprises
a) a CDR4 consisting of the amino acid sequence of SEQ ID 19; and
b) a CDR5 consisting of the amino acid sequence of SEQ ID 17; and
c) a CDR6 consisting of the amino acid sequence of SEQ ID 18;
or B) an antibody which is a functionally active variant of a parent antibody that is any of the group members of A, which comprises at least one functionally active CDR variant of any of the CDR4, CDR5 or CDR6 of the parent antibody.

Specifically, the functionally active variant is a functionally active CDR variant which comprises at least one point mutation in the parent CDR sequence, and comprises or consists of the amino acid sequence that has at least 60% sequence identity with the parent CDR sequence, preferably at least 70%, at least 80%, at least 90% sequence identity.

Specifically, the antibody comprises a VL domain characterized by
a) a CDR4 consisting of the amino acid sequence of SEQ ID 19 or a functionally active CDR variant of the CDR4; and
b) a CDR5 consisting of the amino acid sequence of SEQ ID 20 or a functionally active CDR variant of the CDR5; and
c) a CDR6 consisting of the amino acid sequence of SEQ ID 18 or a functionally active CDR variant of the CDR6;
preferably in combination with any of the VH sequences as described herein.

Specifically, the antibody comprises a VL amino acid sequence selected from any of the VL sequences as depicted in FIG. 2.

Specifically, the antibody comprises both, VH and VL amino acid sequences, and optionally further framework sequences of a full-length antibody or an antibody fragment, in particular any of a full-length antibody or Fab fragment.

Specifically, the antibody comprises
a) the CDR1-CDR6 sequences of any of the antibodies as listed in Table 1; or
b) the VH and VL sequences of any of the antibodies as depicted in FIG. 2; or
c) which is a functionally active variant of a parent antibody that is characterized by the sequences of a)-c), preferably wherein
  i. the functionally active variant comprises at least one functionally active CDR variant of any of the CDR1-CDR6 of the parent antibody; and/or
  ii. the functionally active variant comprises at least one point mutation in the framework region of any of the VH and VL sequences;
  and further wherein
  iii. the functionally active variant has a specificity to bind the same epitope as the parent antibody; and/or
  iv. the functionally active variant is a human, humanized, chimeric or murine and/or affinity matured variant of the parent antibody.

Specifically, the antibody is selected from the group consisting of
a) an antibody comprising
  a. the CDR1 sequence of SEQ ID 1; and
  b. the CDR2 sequence of SEQ ID 2; and
  c. the CDR3 sequence of SEQ ID 3; and
  d. the CDR4 sequence of SEQ ID 13; and
  e. the CDR5 sequence of SEQ ID 14; and
  f. the CDR6 sequence of SEQ ID 15;
b) an antibody comprising
  a. the CDR1 sequence of SEQ ID 4; and
  b. the CDR2 sequence of SEQ ID 5; and
  c. the CDR3 sequence of SEQ ID 6; and
  d. the CDR4 sequence of SEQ ID 16; and
  e. the CDR5 sequence of SEQ ID 17; and
  f. the CDR6 sequence of SEQ ID 18;
c) an antibody comprising
  a. the CDR1 sequence of SEQ ID 7; and
  b. the CDR2 sequence of SEQ ID 8; and
  c. the CDR3 sequence of SEQ ID 9; and
  d. the CDR4 sequence of SEQ ID 19; and
  e. the CDR5 sequence of SEQ ID 20; and
  f. the CDR6 sequence of SEQ ID 18;
d) an antibody comprising
  a. the CDR1 sequence of SEQ ID 10; and
  b. the CDR2 sequence of SEQ ID 11; and
  c. the CDR3 sequence of SEQ ID 12; and
  d. the CDR4 sequence of SEQ ID 19; and
  e. the CDR5 sequence of SEQ ID 17; and
  f. the CDR6 sequence of SEQ ID 18;
e) an antibody comprising
  a. the CDR1 sequence of SEQ ID 4; and
  b. the CDR2 sequence of SEQ ID 5; and
  c. the CDR3 sequence of SEQ ID 6; and
  d. the CDR4 sequence of SEQ ID 19; and
  e. the CDR5 sequence of SEQ ID 20; and
  f. the CDR6 sequence of SEQ ID 18;
and
f) an antibody comprising
  a. the CDR1 sequence of SEQ ID 10; and
  b. the CDR2 sequence of SEQ ID 11; and
  c. the CDR3 sequence of SEQ ID 12; and
  d. the CDR4 sequence of SEQ ID 19; and
  e. the CDR5 sequence of SEQ ID 20; and
  f. the CDR6 sequence of SEQ ID 18;
or a functionally active CDR variant of any of the foregoing, which has an affinity to bind the gal-III antigen with a Kd of less than $10^{-8}$M, preferably less than $10^{-9}$M, preferably less than $10^{-10}$M, preferably less than $10^{-11}$M, e.g. with an affinity in the picomolar range.

Specifically the antibody comprises a functionally active CDR variant of any of the CDR sequences as listed in Table 1, wherein the functionally active CDR variant comprises at least one of
a) 1, 2, or 3 point mutations in the parent CDR sequence; and/or
b) 1 or 2 point mutations in any of the four C-terminal or four N-terminal, or four centric amino acid positions of the parent CDR sequence; and/or
c) at least 60% sequence identity with the parent CDR sequence;
preferably wherein the functionally active CDR variant comprises 1 or 2 point mutations in any CDR sequence consisting of less than 4 or 5 amino acids.

Specifically, the functionally active variant antibody comprises at least one of the functionally active CDR variants of the invention. Specifically, the functionally active variant antibody comprising one or more of the functionally active CDR variants has a specificity to bind the same epitope as the parent antibody.

Specifically, the functionally active variant is a CDR variant, e.g. which comprises a CDR, more specifically a CDR loop sequence, with an amino acid sequence having at least 60% sequence identity, preferably at least 70%, 80% or 90% sequence identity.

According to a specific aspect, the at least one point mutation is any of an amino acid substitution, deletion and/or insertion of one or more amino acids.

Specifically, the functionally active variant differs from the parent antibody in at least one point mutation in the amino acid sequence, preferably in the CDR, wherein the number of point mutations in each of the CDR amino acid sequences is either 0, 1, 2 or 3.

Specifically, the antibody is derived from such antibodies, employing the respective CDR sequences, or CDR mutants, including functionally active CDR variants, e.g. with 1, 2 or 3 point mutations within one CDR loop, e.g. within a CDR length of 5-18 amino acids, e.g. within a CDR region of 5-15 amino acids or 5-10 amino acids. Alternatively, there may be 1 to 2 point mutations within one CDR loop, e.g. within a CDR length of less than 5 amino acids, to provide for an antibody comprising a functionally active CDR variant. Specific CDR sequences might be short, e.g. the CDR2 or CDR5 sequences. According to a specific embodiment, the functionally active CDR variant comprises 1 or 2 point mutations in any CDR sequence consisting of less than 4 or 5 amino acids.

According to a specific aspect, the antibody of the invention comprises CDR and framework sequences, wherein at least one of the CDR and framework sequences includes human, humanized, chimeric, murine or affinity matured sequences, preferably wherein the framework sequences are of an IgG antibody, e.g. of an IgG1, IgG2, IgG3, or IgG4 subtype, or of an IgA1, IgA2, IgD, IgE, or IgM antibody.

Specific antibodies are provided as framework mutated antibodies, e.g. to improve manufacturability or tolerability of a parent antibody, e.g. to provide an improved (mutated) antibody which has a low immunogenic potential, such as humanized antibodies with mutations in any of the CDR sequences and/or framework sequences as compared to a parent antibody.

Further specific antibodies are provided as CDR mutated antibodies, e.g. to improve the affinity of an antibody and/or to target the same epitope or epitopes near the epitope that is targeted by a parent antibody (epitope shift).

Accordingly, any of the antibodies as listed in Table 1 or FIG. 2 may be used as parent antibodies to engineer improved versions.

According to a specific aspect, the antibody of the invention comprises CDR combinations as listed in FIG. 1 (Table 1), provided, that the antibody is still functionally active.

Specifically, the antibody of the invention comprises the CDR1-6 of any of the antibodies as listed in Table 1. However, according to an alternative embodiment, the antibody may comprise different CDR combinations, e.g. wherein an antibody as listed in Table 1 comprises at least one CDR sequence, such as 1, 2, 3, 4, 5, or 6 CDR sequences of one antibody and at least one further CDR sequence of a different antibody of any of the antibodies as listed in Table 1. According to a specific example, the antibody comprises 1, 2, 3, 4, 5, or 6 CDR sequences, wherein the CDR sequences are CDR combinations of more than 1 antibody, e.g. 2, 3, 4, 5, or 6 different antibodies. For example, the CDR sequences may be combined to preferably comprise 1, 2, or all 3 of CDR1-3 of any of the antibodies as listed in Table 1, and 1, 2, or all 3 of CDR4-6 of the same or any other antibody listed in Table 1.

For example, the CDR sequences may be combined to preferably comprise at least CDR1-3 of any of the antibodies as listed in Table 1, e.g. any of the antibodies designated 8E3-E5, 9H9-H7, 5A4-A7, or 2D8-A10 and/or at least CDR4-6 of any (other) of the antibodies as listed in Table 1, e.g. of the antibody designated 5A4-A7, or at least its CDR4 and CDR6 sequences in combination with a functionally active CDR variant of its CDR5. According to a specific embodiment, the antibody of the invention comprises the CDR1-6 of any of the antibodies as listed in Table 1, e.g. any of the antibodies designated 8E3-E5, 9H9-H7, 5A4-A7, or 2D8-A10. However, according to a further specific aspect, the antibody may comprise different CDR combinations, e.g. wherein an antibody as listed in Table 1, e.g. any of the antibodies designated 8E3-E5, 9H9-H7, 5A4-A7, or 2D8-A10 comprises at least one CDR sequence, such as 1, 2, 3, 4, 5, or 6 CDR sequences, of a different antibody, e.g. a CDR sequence of any different antibody of any of the antibodies as listed in Table 1. For example, the antibody comprises 1, 2, 3, 4, 5, or 6 CDR sequences, wherein the CDR sequences are CDR combinations of more than 1 antibody, e.g. 2, 3, 4, 5, or 6 different antibodies. Exemplary antibodies comprising CDR sequences of different antibodies are provided in FIG. 2.

In particular,
i. antibody G3-77 comprises VH-CDR sequences (CDR1, 2, and 3) of antibody 9H9-H7; and VL-CDR sequences (CDR4, 5, and 6) of antibody 5A4-A7;
ii. antibody G3-78 comprises VH-CDR sequences (CDR1, 2, and 3) of antibody 9H9-H7; and VL-CDR sequences (CDR4, 5, and 6) of antibody 5A4-A7;
iii. antibody G3-97 comprises VH-CDR sequences (CDR1, 2, and 3) of antibody 2D8-A10; and VL-CDR sequences (CDR4, 5, and 6) of antibody 5A4-A7.

According to a specific embodiment, the antibody only comprises a VH domain as antigen binding moiety, thus, comprises CDR1-3, without a respective VL domain.

It is herein specifically understood that the CDRs numbered CDR1, 2, and 3 represent the binding region of the VH domain, and CDR4, 5, and 6 represent the binding region of the VL domain.

According to a specific aspect, the antibody of the invention comprises any of the VH and VL amino acid sequence combinations as depicted in FIG. 2, or the binding site formed by such combination of VH and VL amino acid sequences. Alternatively, combinations of the immunoglobulin domains of two different antibodies may be used, provided, that the antibody is still functionally active. For example, the VH sequence of one antibody may be combined with a VL sequence of another antibody. According to further specific embodiments, any of the framework regions as provided in FIG. 2 may be employed as a framework to any of the CDR sequences and/or VH/VL combinations as described herein.

According to a specific aspect, the antibody of the invention comprises any of the VH and VL amino acid sequence combinations as depicted in FIG. 2, or the binding site formed by such combination of VH and VL amino acid sequences.

It is understood that the antibody of the invention optionally comprises such amino acid sequences of FIG. 2 with or without a suitable signal or leader sequence.

According to a specific aspect, each of the sequences of FIG. 2 may be terminally extended or deleted in the constant region, e.g. a deletion of one or more of the C-terminal amino acids.

FIG. 2 shows different VH sequences and different VL sequences of parent antibodies referred to as 8E3-E5, 9H9-H7, 5A4-A7, 2D8-A10, G3-43, G3-46, G3-77, G3-78, and G3-97, and supports any VH/VL combination, thus a series of different VH/VL combinations for each of the parent antibodies, e.g. such as depicted in FIG. 9. Therefore, specific variants of a parent antibody may include a VH sequence of one parent antibody and a VL sequence of another parent antibody, or a combination of functionally active variants of such VH and VL sequences, e.g. functionally active variants that derive from the same parent antibody.

In particular, FIG. 2 shows different VH sequences and different VL sequences of the parent antibodies referred to as 8E3-E5, 9H9-H7, 5A4-A7, 2D8-A10, G3-43, G3-46, G3-77, G3-78, and G3-97. For example, 81 different VH/VL combinations are feasible combining a VH sequence of one parent antibody and a VL sequence of another parent antibody, and many more variants are possible, if any of the VH or VL sequences is a functionally active variant of the parent sequence, e.g. a variant which includes any of a CDR mutation and/or a framework mutation.

The CDR sequences included in the VH and VL sequences of FIG. 2 are identical to the respective CDR sequences as listed in FIG. 1.

The invention further provides for a method of producing functionally active antibody variants of a parent antibody which is any of the antibodies of the invention, e.g. an antibody as listed in Table 1, or comprising any of the VH or VL amino acid sequence combinations as depicted in FIG. 2, or comprising the binding site formed by such combination of VH and VL amino acid sequences, which method comprises engineering at least one point mutation in any of the framework regions (FR) or constant domains, or complementarity determining regions (CDR1 to CDR6) to obtain a variant antibody, and determining the functional activity of the variant antibody, specifically by the affinity to bind the gal-III epitope with a Kd of less than $10^{-6}$M, preferably less than $10^{-7}$M, or less than $10^{-8}$M, or less than $10^{-9}$M, even less than $10^{-10}$M, or less than $10^{-11}$M, e.g. with an affinity in the picomolar range. Upon determining the functional activity, the functionally active variants are selected for further use and optionally for production by a recombinant production method.

According to a specific aspect, the variant antibody binds the same epitope as the parent antibody.

According to a further specific aspect, the variant antibody comprises the same binding site as the parent antibody.

Functionally active variant antibodies may differ in any of the VH or VL sequences, or share the common VH and VL sequences, and comprise modifications in the respective FR. The variant antibody derived from the parent antibody by mutagenesis may be produced a methods well-known in the art.

Exemplary parent antibodies are described in the examples section below and in FIG. 1 (Table 1) and FIG. 2. Specifically, the antibody is a functionally active derivative of a parent antibody that is characterized by the sequences as listed in Table 1 or FIG. 2. Variants with one or more modified CDR sequences, and/or with one or more modified FR sequences, such as sequences of FR1, FR2, FR3 or FR4, or a modified constant domain sequence may be engineered.

For example, functionally active variant antibodies may be obtained by mutagenesis, specifically by affinity maturation and/or humanization. Though the variant antibodies may still share common CDR sequences CDR1-6 or common VH and VL sequences of a parent antibody, it is feasible that also variant antibodies or antibody domains are produced, e.g. with modifications in the respective FR or CDR sequences, which are functionally active.

Exemplary variant antibodies of a parent antibody comprise at least one point mutation in any of the CDR1-CDR6, and/or at least one point mutation in any of the FR sequences, preferably wherein the antibody has a specificity to bind the same epitope as the parent antibody.

In certain aspects, the invention provides for such functionally active variant antibodies, preferably monoclonal antibodies, most preferably humanized or human antibodies, comprising a heavy chain and a light chain, wherein any of the light chain or VL variable region or the respective CDRs comprises an amino acid sequence as derived from a parent antibody, which is the antibody designated 8D5-1G10 or 4D5-D4 or any other antibody as listed in Table 1 or FIG. 2, by modification of at least one FR or CDR sequences.

The invention further provides for an antibody of the invention, for use in treating a subject at risk of or suffering from *Klebsiella pneumoniae* infection or colonization comprising administering to the subject an effective amount of the antibody to limit the infection in the subject or to ameliorate a disease condition resulting from said infection, preferably for treatment or prophylaxis of any of primary and secondary bacteremia, pneumonia, urinary tract infection, liver abscess, peritonitis, or meningitis.

Accordingly, the invention further refer to a method of treating a subject at risk of or suffering from *Klebsiella pneumoniae* infection or colonization comprising administering to the subject an effective amount of the antibody to limit the infection in the subject or to ameliorate a disease condition resulting from said infection, preferably for treatment or prophylaxis of any of primary and secondary bacteremia, pneumonia, urinary tract infection, liver abscess, peritonitis, or meningitis.

The antibody is specifically able to neutralize lethal endotoxemia. Such functional activity may be determined in an appropriate in vivo model (challenge with purified LPS).

Specifically, the antibody may provide bactericidal activity against *Klebsiella pneumoniae* of the gal-III O-type, in particular MDR *Klebsiella pneumoniae*, preferably MDR *Klebsiella pneumoniae* ST258.

According to a specific aspect, immunotherapy using the antibody of the invention may effectively protect against live bacterial challenge, e.g. as determined in various animal models.

The antibody can be specifically effective against *Klebsiella pneumoniae* of the gal-III O-type by complement-mediated killing, e.g. as determined by an in vitro serum bactericidal assay (SBA), e.g. with at least 20% killing of bacteria above the control samples (no antibody or irrelevant control mAb added).

The antibody can be specifically effective against *Klebsiella pneumoniae* of the gal-III O-type by antibody mediated phagocytosis, e.g. as determined by an in vitro opsonophagocytotic killing assay (OPK), e.g. with at least 20% uptake of input bacteria or 20% lower end CFU count above the control samples (no antibody or irrelevant control mAb added).

The antibody is specifically effective against *Klebsiella pneumoniae* of the gal-III O-type by neutralizing endotoxin functions, e.g. as determined by an in vitro LAL assay, or toll-like receptor 4 (TLR4) reporter assay e.g. with at least 20% reduction in endotoxin activities in comparison to control samples (no antibody or irrelevant control mAb added).

According to a further specific aspect, the antibody neutralizes the targeted pathogen in animals, including both, human and non-human animals, and inhibits pathogenesis in vivo, preferably any models of primary and secondary bacteremia, pneumonia, urinary tract infection, liver abscess, peritonitis, or meningitis.

As a reference (positive control) for determining the neutralization potency, any of the antibodies described in the examples section may be use. Preferably, the neutralization potency of an antibody of the invention is equal or higher than the antibody characterized by the CDR1-6 sequences of the antibody herein referred to as 2D8-A10, in particular the chimeric IgG1 antibody as described in the Examples.

The invention further provides for a pharmaceutical preparation comprising the antibody of the invention, preferably comprising a parenteral or mucosal formulation, optionally containing a pharmaceutically acceptable carrier or excipient.

Such pharmaceutical composition may contain the antibody as the sole active substance, or in combination with other active substances, or a cocktail of active substances, such as a combination or cocktail of at least two or three different antibodies.

According to the invention, the antibody of the invention is specifically provided for medical, diagnostic or analytical use.

The invention further provides for the use of the antibody of the invention for diagnostic purposes, specifically for the diagnosis of *Klebsiella pneumoniae* (especially ST258) infection or colonization, or an associated disease such as primary and secondary bacteremia, pneumonia, urinary tract infection, liver abscess, peritonitis, or meningitis in a subject.

Specifically, the subject is a human being, in particular an immunocompromised or immunosuppressed patient, or a contact thereof.

Specifically, the antibody is provided for use according to the invention, wherein a systemic infection or colonization with *Klebsiella pneumoniae* of the gal-III O-type in a subject is determined ex vivo by contacting a biological sample of said subject with the antibody, wherein a specific immune reaction of the antibody determines the infection or colonization.

Specifically, the biological samples is a body fluid or tissue sample, preferably a sample selected from the group consisting of a blood sample, stool sample, skin sample, urine sample, cerebrospinal fluid, and a respiratory tract specimen such as endotracheal aspirates, pleural fluid, lung tap, nasal swab or sputum, or a *Klebsiella pneumoniae* isolate originating from any of the foregoing. Specifically, a sample of body fluid is tested for the specific immune reaction, which sample is selected from the group consisting of urine, blood, blood isolates or blood culture, aspirate, sputum, lavage fluid of intubated subjects and stool.

Specifically, the biological sample is treated to produce a *Klebsiella pneumoniae* isolate originating from the biological sample, which isolate may be further characterized for its gal-III genotype or phenotype, and/or the level of gal-III antigen expression. Preferable sample preparation methods for producing bacterial isolates are employing bacterial enrichment and cultivation steps.

Specifically, the biological sample is treated to determine the gal-III level directly in the sample, optionally following preparatory steps of enrichment or purification to reduce matrix effects and to increase the specificity and sensitivity of the test. Preparatory steps include culturing of the biological specimen according to standard culture procedures such as but not exclusively being hemocultures in standard growth media as well as the culturing of specimens on solid agar (including phenotyping—i.e. antibiogram) as performed in routine microbiology laboratories. Bacteria may be sub-cultured for expansion of CFU in different growth media (standard media and/or chemically defined media; high nutrient, low nutrient, limited growth media composition) to enhance expression of virulence factors Bacterial suspensions may be prepared and washed in standard buffer solutions to remove potential matrix effects.

Specifically, the gal-III antigen is determined by at least one of an immunoassay, preferably any of ELISA, CIA, RIA, IRMA, agglutination assay, immunochromatography, dipstick assay and Western-blot, or mass-spectrometry, nuclear magnetic resonance (NMR), or a method of determining corresponding DNA or RNA indicative of gal-III expression, in particular determining a nucleic acid sequence specific to the gtr genes, preferably employing a nucleic acid hybridization assay or a nucleic acid amplification assay.

Specifically, the diagnostic use according to the invention refers to determining the serotype of *Klebsiella pneumoniae* in vitro from a pure *Klebsiella pneumoniae* culture recovered from a clinical specimen, to determine whether the bacterium is of the gal-III O-type, or not.

The invention further provides for a diagnostic preparation of the antibody of the invention, comprising the antibody and a further diagnostic reagent in a composition or a kit of parts, comprising the components
 a) the antibody; and
 b) the further diagnostic reagent;
 c) and optionally a solid phase to immobilize at least one of the antibody and the diagnostic reagent.

The diagnostic preparation optionally comprises the antibody of the invention and the further diagnostic reagent in a composition or a kit of parts.

The diagnostic kit preferably comprises all essential components to determine the gal-III expression in the biological sample, optionally without common or unspecific substances or components, such as water, buffer or excipients. The storage stable kit can be stored preferably at least 6 months, more preferably at least 1 or 2 years. It may be composed of dry (e.g. lyophilized) components, and/or include preservatives.

The preferred diagnostic kit is provided as a packaged or prepackaged unit, e.g. wherein the components are contained in only one package, which facilitates routine experiments. Such package may include the reagents necessary for one or more tests, e.g. suitable to perform the tests of a series of biological samples. The kit may further suitably contain a gal-III antigen preparation as a standard or reference control.

The diagnostic composition may be a reagent ready-to-use in a reaction mixture with the biological sample, or a conserved form of such reagent, e.g. a storage-stable form such as lyophilized; snap-frozen (e.g. in liquid nitrogen), ultra low-temperature storage ($-70°$ C. and $-80°$ C.), cold-storage ($-20°$ C. and $5°$ C.) and controlled room temperature ($15°$ C.-$27°$ C.); standard sample storage as e.g. glycerol-stocks, tissue paraffin-blocks, (buccal) swabs and other standard biological sample storage methods, which conserved form of a reagent can be reconstituted or prepared to obtain a ready-to-use reagent. Such ready-to-use reagent is typically in the form of an aqueous solution, specifically (physiological) buffer conditions (e.g. EDTA buffered, phosphate buffer, HBSS, citrate buffer etc.).

Specifically, the further diagnostic reagent is a reagent specifically reacting with the antibody and/or the reaction product of the antibody binding to its antigen. An appropriate diagnostic reagent is suitably used for performing an immunoassay for diagnosing or monitoring, in a subject, the

*Klebsiella pneumoniae* infection or colonization. The appropriate diagnostic reagent can be a solvent, a buffer, a dye, an anticoagulant, a ligand that specifically binds to the antibody of the invention and/or the antibody-antigen immune complex.

Specifically, the invention provides for a diagnostic preparation of an antibody of the invention, optionally containing the antibody with a label and/or a further diagnostic reagent with a label, such as a reagent specifically recognizing the antibody or an immune complex of the antibody with the respective target antigen, and/or a solid phase to immobilize at least one of the antibody and the diagnostic reagent.

The antibody or the diagnostic reagent can be directly labeled or indirectly labeled. The indirect label may comprise a labeled binding agent that forms a complex with the antibody or diagnostic reagent to the gal-III antigen.

The label is typically a molecule or part of a molecule that can be detected in an assay. Examplary labels are chromophores, fluorochromes, or radioactive molecules. In some embodiments the antibody or diagnostic reagent is conjugated to a detectable label which may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preferred diagnostic preparations or assays comprise the antibody of the invention immobilized on a solid phase, e.g. latex beads, gold particles, etc., e.g. to test agglutination by the antibody of bacteria of the gal-III type obtained from a sample to be tested.

The invention further provides for a method of diagnosing *Klebsiella pneumoniae* infection or colonization in a subject caused by a *Klebsiella pneumoniae* strain, comprising
  a) providing an antibody according to the invention, and
  b) detecting if the antibody specifically immunoreacts with the galactan-III epitope in a biological sample of the subject to be tested, thereby diagnosing *Klebsiella pneumoniae* infection or colonization.

Such diagnosis is specifically indicated in case of a MDR *Klebsiella pneumoniae* infection of colonization, in particular addressing MDR *Klebsiella pneumoniae* of the gal-III type. Optionally, a diagnostic assay may involve two different antibodies with different specificity and/or affinity to bind gal-III and/or gal-I, so to possibly differentiate between the gal-III and gal-I antigens.

According to a specific aspect, the invention provides for companion diagnostics to determine the infection of a subject with *Klebsiella pneumoniae*, in particular with MDR *Klebsiella pneumoniae*, by the diagnostics of the invention or the diagnostic method of the invention, to provide for the basis of treatment with a therapeutic against such infection, e.g. employing immunotherapy, such as treating with an antibody of the invention.

According to a specific aspect, the invention provides for a sensitive bedside diagnostics to diagnose infection of a subject with *Klebsiella pneumoniae*, in particular with MDR *Klebsiella pneumoniae*, by determining free LPS, e.g. from clinical specimen where the amount of live bacteria is limited. The sensitivity of such assay is specifically less than 100 ng preferably less than 10 ng of LPS.

The invention further provides for an isolated nucleic acid encoding an antibody of any of the invention.

The invention further provides for an expression cassette or a plasmid comprising a coding sequence to express a protein comprising a VH and/or VL of an antibody of the invention.

The invention further provides for a host cell comprising an expression cassette or a plasmid of the invention.

The invention further provides for a method of producing an antibody of the invention, wherein a host cell of the invention is cultivated or maintained under conditions to produce said antibody.

Specifically preferred is a host cell and a production method employing such host cell, which host cell comprises
  the plasmid or expression cassette of the invention, which incorporates a coding sequence to express the antibody light chain; and
  the plasmid or expression cassette of the invention, which incorporates a coding sequence to express the antibody heavy chain.

According to a further aspect, the invention provides for a method of producing an antibody of the invention, comprising
  a) immunizing a non-human animal with the gal-III antigen of *Klebsiella pneumoniae* and isolating B-cells producing antibodies;
  b) forming immortalized cell lines from the isolated B-cells;
  c) screening the cell lines to identify a cell line producing a monoclonal antibody that specifically binds to the gal-III antigen and optionally the gal-I antigen, e.g. wherein preferential binding to gal-III as compared to gal-I is determined; and
  d) producing the monoclonal antibody, or a humanized or human form of the antibody, or a derivative thereof with the same epitope binding specificity as the monoclonal antibody.

The invention further provides for a method of identifying a candidate antibody comprising:
  a) providing a sample containing an antibody or antibody-producing cell; and
  b) assessing for binding of an antibody in or produced by the sample with a galactan-III epitope, wherein a positive reaction between the antibody and the epitope identifies the antibody as candidate antibody.

The invention further provides for a method of identifying a candidate antibody comprising:
  a) providing a sample containing an antibody or antibody-producing cell; and
  b) assessing for binding of an antibody in or produced by the sample with the galactan-III epitope, wherein a specific positive reaction between the antibody and the galactan-III epitope relative to the galactan-I epitope identifies the antibody as candidate antibody.

The invention further provides for a method of producing an antibody of the invention, comprising
  a) providing a candidate antibody identified according to the invention; and
  b) producing a monoclonal antibody, or a humanized or human form of the candidate antibody, or a derivative thereof with the same epitope binding specificity as the candidate antibody.

FIGURES

FIG. 1. Table 1: CDR sequences (Kabat nomenclature) of antibodies designated as 8E3-E5, 9H9-H7, 5A4-A7, and 2D8-A10.

The nomenclature as used in FIG. 1 shall have the following meaning:
VH CDR1=CDR1
VH CDR2=CDR2
VH CDR3=CDR3
VL CDR4=CDR4=VL CDR1
VL CDR5=CDR5=VL CDR2
VL CDR6=CDR6=VL CDR3

FIG. 2. VH and VL sequences of
Chimeric antibodies (with mouse variable domains) 8E3-E5, 9H9-H7, 5A4-A7, and 2D8-A10, including the CDR sequences of Table 1 and framework sequences.
Humanized antibodies G3-43, G3-46, G3-77, G3-78, G3-97
G3-43 VH: (including CDR sequences of VH 5A4-A7)
G3-43 VL: (including CDR sequences of VL 5A4-A7)
G3-46 VH: (including CDR sequences of VH 5A4-A7)
G3-46 VL: (including CDR sequences of VL 5A4-A7)
G3-77 VH: (including CDR sequences of VH 9H9-H7)
G3-77 VL: (including CDR sequences of VL 5A4-A7)
G3-78 VH: (including CDR sequences of VH 9H9-H7)
G3-78 VL: (including CDR sequences of VL 5A4-A7)
G3-97 VH: (including CDR sequences of VH 2D8-A10)
G3-97 VL: (including CDR sequences of VL 5A4-A7)
FR sequences of the VH: FR1 (located N-terminal to CDR1), FR2 (located between CDR1 and CDR2), FR3 (located between CDR2 and CDR3) and FR4 (located C-terminal to CDR3).
FR sequences of the VL: FR1 (located N-terminal to CDR4), FR2 (located between CDR4 and CDR5), FR3 (located between CDR5 and CDR6) and FR4 (located C-terminal to CDR6).

FIG. 3. Schematic structure and sugar composition of the *K. pneumoniae* O1, O2ab and O2ac O-antigen side chains. Based on the present invention, galactan-I subunits may be replaced by galactan-III subunits at all instances.

FIG. 4. Length of the rfb (wb) operon in sequenced *K. pneumoniae* strains (A) and schematic comparison of genetic organization of the different rfb (wb) loci encoding galactan-I (B). Genes depicted as black designate the ones described by Clarke et al. (3). Empty arrows represent the gtr-like genes, while the grey arrows between the two rfb (wb) variants stand for the non-conserved hypothetical glycosyltransferase genes.

Figure 5:
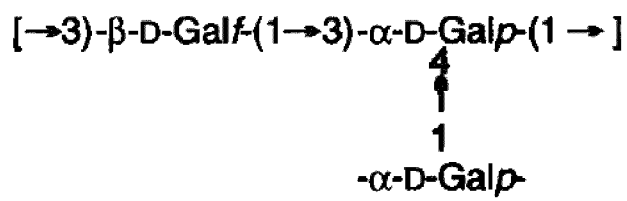

FIG. 5. Structure of the modified galactan-I (termed herein as galactan-III) repeating units (5).

Figure 6:
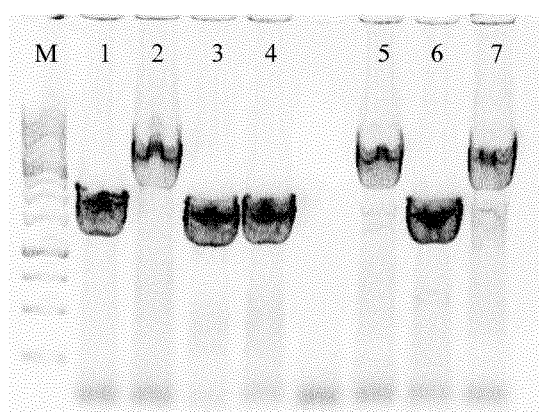

FIG. 6. Result of PCR reaction detecting gtr-like genes in rfb (wb) operon of O1, O2 and O2ac. Amplicon with ~2 kb size confirms lack of gtr-like genes, however amplicon with ~5 kb suggests the presence of gtr-like genes between wbbO and hisI.

Figure 7:
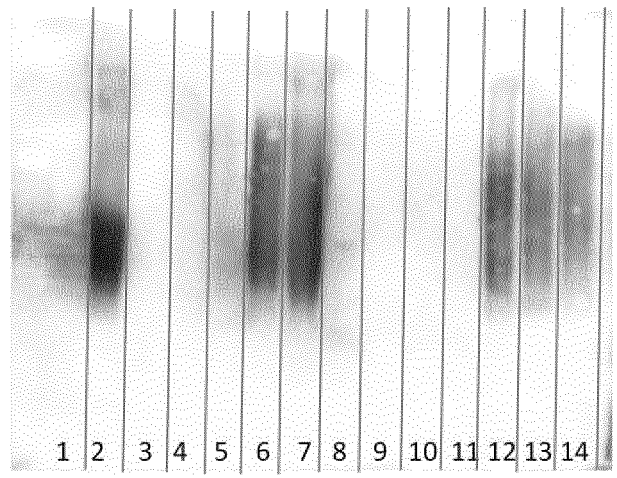

FIG. 7. Immunoblot with mAb 9H9-H7 recognizing D-galactan III molecules.

Figure 8:
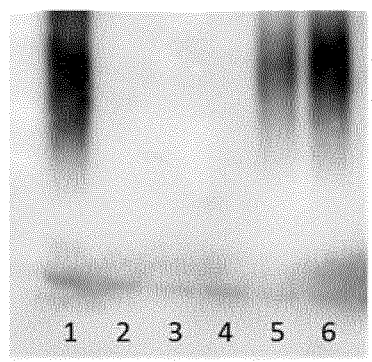

FIG. 8. Immunoblot using LPS purified from an isogenic panel of strains confirms reactivity of mAbs with the presence of gtr genes.

FIG. 9. VH and VL composition of humanized mAbs tested. CDR regions of the humanized mAbs originate from the indicated chimeric parents. The indicated CDR regions were grafted into human framework sequences. Retained binding characteristics of humanized mAbs was confirmed by surface staining of gal-III expressing *K. pneumoniae* measured by flow cytometry (last columns).

FIG. 10. Protection elicited by chimeric (panel A) or humanized (panel B) galactan-III specific mAbs (1 or 2 μg/mouse doses, respectively) against a subsequent lethal challenge by live *K. pneumoniae* in the GalN sensitized mouse model of bacteraemia. Graph shows combined results of two individual experiments with groups of 5 mice each.

Figure 11:
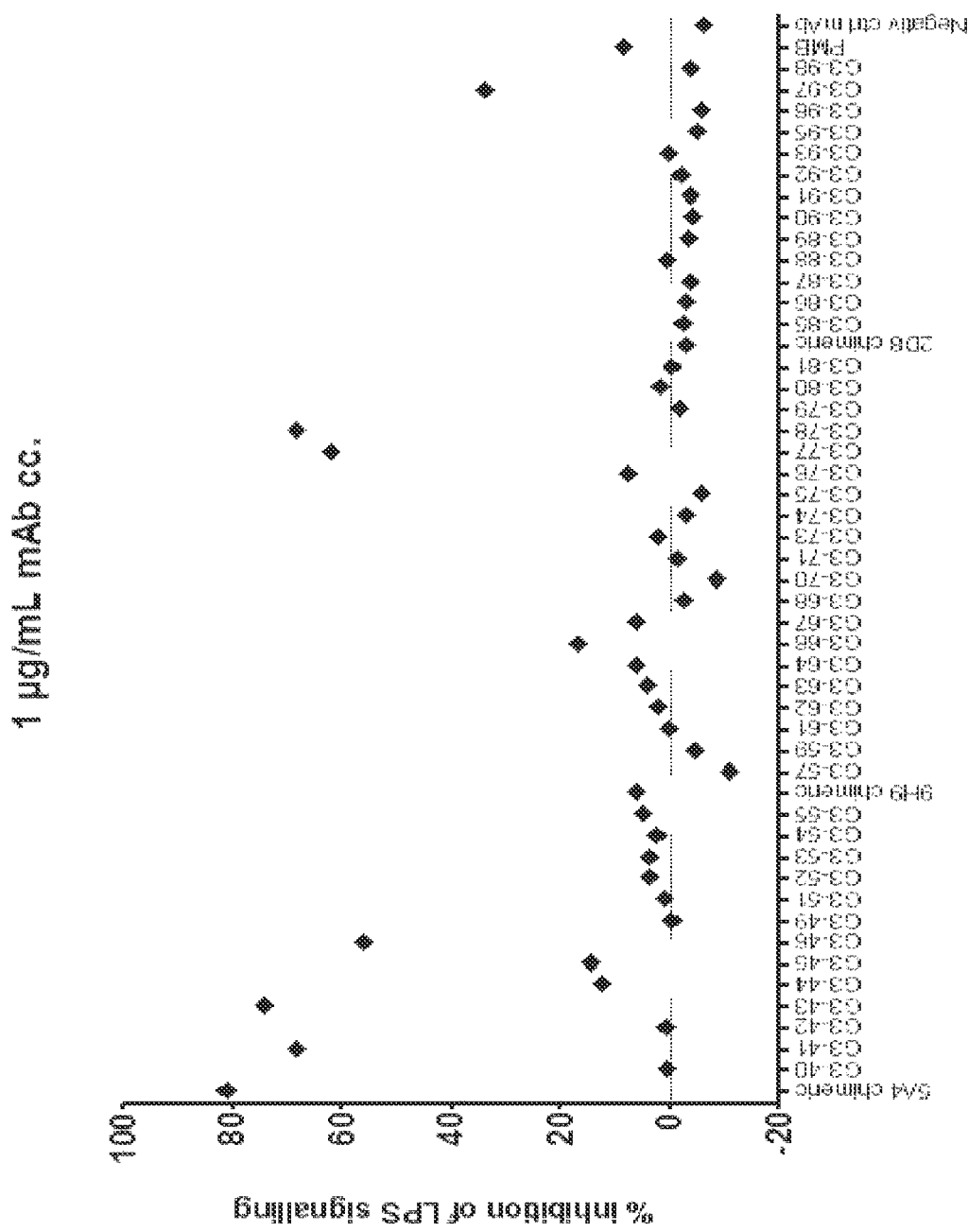

FIG. 11. Endotoxin neutralization potential of humanized gal-III specific mAbs at 1 μg/ml concentration. See details in the text.

Figure 12:
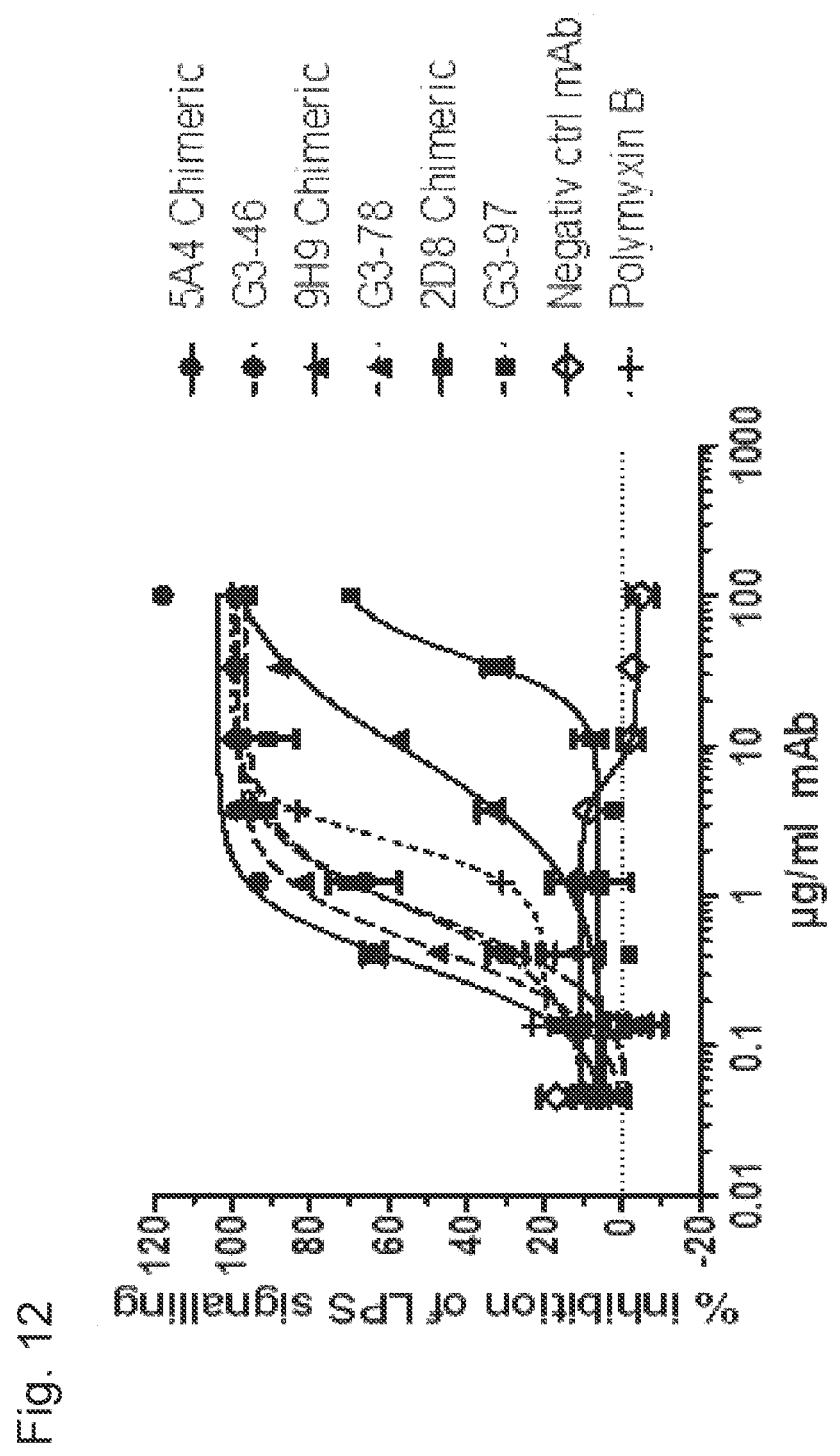

FIG. 12. Dose titration of endotoxin neutralization potential exhibited by selected humanized and parental chimeric gal-III specific mAbs. As a benchmark neutralization by polymyxin B was used.

DETAILED DESCRIPTION OF THE INVENTION

The term "antibody" as used herein shall refer to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody as used herein has a specific binding site to bind one or more antigens or one or more epitopes of such antigens, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)$_2$, scFv, Fv, or a full length antibody.

The term "antibody" as used herein shall particularly refer to antibody formats comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody, e.g. of an IgG type (e.g., an IgG1, IgG2, IgG3, or IgG4 sub-type), IgA1, IgA2, IgD, IgE, or IgM antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall specifically include antibodies in the isolated form, which are substantially free of other antibodies directed against different target antigens or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies of animal origin, including human species, such as mammalian, including human, murine, rabbit, goat, lama, cow and horse, or avian, such as hen, which term shall particularly include recombinant antibodies which are based on a sequence of animal origin, e.g. human sequences.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" may further apply to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term "antibody" specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused at any position of one or more other proteins, such as other antibodies, e.g. a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof (e.g. PEG, prodrugs or drugs). In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g. radioisotope labels or fluorescent labels, or, in the case of an enzymatic label, may catalyze chemical alteration of a substrate compound or composition which is detectable.

The preferred derivatives as described herein are functionally active with regard to the antigen binding, preferably which have a potency to combat *K. pneumonia*, e.g. as determined in an SBA, OPK or LAL assay, or to protect against bacterial challenge or to neutralize endotoxemia.

Specifically, an antibody derived from an antibody of the invention may comprise at least one or more of the CDR regions or CDR variants thereof being functionally active in differentially binding to the gal-III antigen, e.g. specifically or selectively binding the gal-III antigen.

Antibodies derived from a parent antibody or antibody sequence, such as a parent CDR or FR sequence, are herein particularly understood as mutants or variants obtained by e.g. in silico or recombinant engineering or else by chemical derivatization or synthesis.

It is understood that the term "antibody" also refers to variants of an antibody, including antibodies with functionally active CDR variants of a parent CDR sequence, and functionally active variant antibodies of a parent antibody.

Specifically, an antibody derived from an antibody of the invention may comprise at least one or more of the CDR regions or CDR variants thereof, e.g. at least 3 CDRs of the heavy chain variable region and/or at least 3 CDRs of the light chain variable region, with at least one point mutation in at least one of the CDR or FR regions, or in the constant region of the HC or LC, being functionally active, e.g. specifically binding the gal-III antigen.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatize an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomization techniques. In some cases positions are chosen randomly, e.g. with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "variant" shall specifically encompass functionally active variants.

The term "functionally active variant" of a CDR sequence as used herein, is understood as a "functionally active CDR variant", and the "functionally active variant" of an antibody as used herein, is understood as "functionally active antibody variant". The functionally active variant means a sequence resulting from modification of this sequence (a parent antibody or a parent sequence) by insertion, deletion or substitution of one or more amino acids, or chemical derivatization of one or more amino acid residues in the amino acid sequence, or nucleotides within the nucleotide sequence, or at either or both of the distal ends of the sequence, e.g. in a CDR sequence the N-terminal and/or C-terminal 1, 2, 3, or 4 amino acids, and/or the centric 1, 2, 3, or 4 amino acids (i.e. in the midst of the CDR sequence), and which modification does not affect, in particular impair, the activity of this sequence. In the case of a binding site having specificity to a selected target antigen, the functionally active variant of an antibody would still have the predetermined binding specificity, though this could be changed, e.g. to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active CDR variant.

Specifically, the functionally active variants of an antibody of the invention have the potency to bind gal-III antigen and the specificity or selectivity to preferentially bind to the gal-III antigen relative to other antigens of *K. pneumoniae*, e.g. binding to gal-III and not binding to the gal-I antigen of *K. pneumoniae*, or not significantly binding the gal-I antigen, and/or not binding to other antigens of *K. pneumoniae*.

Functionally active variants may be obtained, e.g. by changing the sequence of a parent antibody, e.g. an antibody comprising the same binding site as any of the antibodies as listed in Table 1 and FIG. 2, but with modifications within an antibody region besides the binding site, or derived from such parent antibody by a modification within the binding site but that does not impair the antigen binding, and preferably would have substantially the same biological activity as the parent antibody or even an improved activity, including the ability to specifically or selectively bind gal-III antigen, e.g. binding to gal-III and not binding to the gal-I antigen of *K. pneumoniae*, or not significantly binding the gal-I antigen, and/or not binding to other antigens of *K. pneumoniae*. Optionally, the functionally active variants may further include a neutralizing potency and/or a potency of complement mediated killing in an SBA assay, and/or optionally further include a potency of an antibody mediated phagocytosis in an OPK assay, and/or optionally further include endotoxin neutralization function in a LAL assay, e.g. with substantially the same biological activity, as determined by the specific binding assay or functional test to target (MDR) *K. pneumoniae*.

The term "substantially the same biological activity" as used herein refers to the activity as indicated by substantially the same activity being at least 20%, at least 50%, at least 75%, at least 90%, e.g. at least 100%, or at least 125%, or at least 150%, or at least 175%, or e.g. up to 200%, or even a higher activity as determined for the comparable or parent antibody.

The preferred variants or derivatives as described herein are functionally active with regard to the antigen binding, preferably which have a potency to specifically bind gal-III antigen, and not binding to other antigens of *K. pneumoniae*, e.g. binding to gal-III and not binding to the gal-I antigen of *K. pneumoniae*, or not significantly binding the gal-I antigen, or preferentially binding the gal-III antigen relative to gal-I, or binding the gal-III with higher affinity as compared to current polyclonal typing sera raised against gal-I strains. Preferred variants are not binding to other antigens of *K. pneumoniae*, with a Kd value difference of at least 2 logs, preferably at least 3 logs, and optionally further including a potency of complement mediated killing in an SBA assay, e.g. to achieve significant reduction in bacterial counts relative to control samples not containing the antibody, and/or optionally further including a potency of an antibody mediated phagocytosis in an OPK assay, such as to achieve significant reduction in bacterial counts relative to control samples not containing the antibody, and/or optionally further including endotoxin neutralization function in a LAL or TLR4 signaling assay, such as to achieve significant reduction of endotoxin activity relative to control samples not containing the antibody, e.g. with substantially the same biological activity, as determined by the specific binding assay or functional test to target *K. pneumoniae*. The significant reduction of activity in the various assays typically means the reduction of at least 50%, preferably at least 60%, 70%, 80%, 90%, 95% or 98% up to complete reduction of about 100% (+/−1%).

In a preferred embodiment the functionally active variant of a parent antibody a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;

b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the antibody or a functionally active variant thereof and additionally at least one amino acid or nucleotide heterologous to the polypeptide or the nucleotide sequence.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

Specific functionally active variants are CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:
  Alanine: (Ala, A) nonpolar, neutral;
  Asparagine: (Asn, N) polar, neutral;
  Cysteine: (Cys, C) nonpolar, neutral;
  Glutamine: (Gln, Q) polar, neutral;
  Glycine: (Gly, G) nonpolar, neutral;
  Isoleucine: (Ile, I) nonpolar, neutral;
  Leucine: (Leu, L) nonpolar, neutral;
  Methionine: (Met, M) nonpolar, neutral;
  Phenylalanine: (Phe, F) nonpolar, neutral;
  Proline: (Pro, P) nonpolar, neutral;
  Serine: (Ser, S) polar, neutral;
  Threonine: (Thr, T) polar, neutral;
  Tryptophan: (Trp, W) nonpolar, neutral;
  Tyrosine: (Tyr, Y) polar, neutral;
  Valine: (Val, V) nonpolar, neutral; and
  Histidine: (His, H) polar, positive (10%) neutral (90%).

The "positively" charged amino acids are:
  Arginine: (Arg, R) polar, positive; and
  Lysine: (Lys, K) polar, positive.

The "negatively" charged amino acids are:
  Aspartic acid: (Asp, D) polar, negative; and
  Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g. produced by glycoengineering, which are functional and may serve as functional equivalents, e.g. binding to the specific targets and with functional properties.

An antibody of the present invention may or may not exhibit Fc effector function. Though the mode of action is mainly mediated by neutralizing antibodies without Fc effector functions, Fc can recruit complement and aid elimination of the target antigen, such as a toxin, from the circulation via formation of immune complexes.

Specific antibodies may be devoid of an active Fc moiety, thus, either composed of antibody domains that do not contain an Fc part of an antibody or that do not contain an Fc gamma receptor binding site, or comprising antibody domains lacking Fc effector function, e.g. by modifications to reduce Fc effector functions, in particular to abrogate or reduce ADCC and/or CDC activity. Alternative antibodies may be engineered to incorporate modifications to increase Fc effector functions, in particular to enhance ADCC and/or CDC activity.

Such modifications may be effected by mutagenesis, e.g. mutations in the Fc gamma receptor binding site or by derivatives or agents to interfere with ADCC and/or CDC activity of an antibody format, so to achieve reduction or increase of Fc effector function.

A significant reduction of Fc effector function is typically understood to refer to Fc effector function of less than 10% of the unmodified (wild-type) format, preferably less than 5%, as measured by ADCC and/or CDC activity. A significant increase of Fc effector function is typically understood to refer to an increase in Fc effector function of at least 10% of the unmodified (wild-type) format, preferably at least 20%, 30%, 40% or 50%, as measured by ADCC and/or CDC activity.

The term "glycoengineered" variants with respect to antibody sequences shall refer to glycosylation variants having modified immunogenic or immunomodulatory (e.g. anti-inflammatory) properties, ADCC and/or CDC, as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC). Removal of N-Glycan at N297, e.g. through mutating N297, e.g. to A, or T299 typically results in aglycosylated antibody formats with reduced ADCC. Specifically, the antibody of the invention may be glycosylated or glycoengineered, or aglycosylated antibodies.

Major differences in antibody glycosylation occur between cell lines, and even minor differences are seen for a given cell line grown under different culture conditions. Expression in bacterial cells typically provides for an aglycosylated antibody. CHO cells with tetracycline-regulated expression of $\beta(1,4)$-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180). In addition to the choice of host cells, factors that affect glycosylation during recombinant production of antibodies include growth mode, media formulation, culture density, oxygenation, pH, purification schemes and the like.

The term "antigen-binding site" or "binding site" refers to the part of an antibody that participates in antigen binding. The antigen binding site is formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are interposed between more conserved flanking stretches known as framework regions, The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "antigen" as used herein interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. Specific antigens like the gal-III or gal-I antigens are carbohydrate structures and may be provided as isolated antigens optionally provided on an artificial carrier, or else in the form of K. pneumoniae cells expressing the antigens or cell fractions thereof.

The term "epitope" as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping.

Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the single epitope recognized by an antibody, or a cross-reactive epitope which is shared by at least two different antigens and optionally recognized by the cross-reactive antibody.

The term "expression" is understood in the following way. Nucleic acid molecules containing a desired coding sequence of an expression product such as e.g. an antibody as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those which are not naturally occurring, e.g. codon-optimized nucleic acids or cDNA, or chemically synthesized.

Likewise, the isolated antibody of the invention is specifically non-naturally occurring, e.g. as provided in a combination preparation with another antibody or active agent, which combination does not occur in nature, or an optimized or affinity-maturated variant of a naturally occurring antibody, or an antibody with a framework-region which is engineered to improve the manufacturability of the antibody. By such optimizing or engineering the antibody comprises one or more synthetic sequences or characteristics, which would not be found in the context of the antibody in nature.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated antibodies or epitopes of the invention, the term "isolated" shall specifically refer to compounds that are free or substantially free of material with which they are naturally associated such as other compounds with which they are found in their natural environment, or the environment in which they are prepared (e.g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy. In particular, the isolated antibody of the invention differs from polyclonal serum preparations raised against K. pneumoniae strains, because it is provided in the isolated and purified form, preferably provided in a preparation comprising the isolated antibody as the only active substance. This does not preclude, however, that the isolated antibody is provided in a combination product comprising a limited number of further well-defined (isolated) antibodies. Isolated antibodies may as well be provided on a solid, semi-liquid or liquid carrier, such as beads.

The term "neutralizing" or "neutralization" is used herein in the broadest sense and refers to any molecule that inhibits a pathogen, such as K. pneumoniae from infecting a subject, or to inhibit the pathogen from promoting infections by producing endotoxins, or to inhibit the endotoxins from exerting their biological activity, irrespective of the mechanism by which neutralization is achieved. Neutralization can be achieved, e.g., by an antibody that inhibits the colonization by K. pneumoniae of mucosal surfaces, invasion to sterile body sites, and eliciting adverse biological signals (in worst case inducing septic shock) in the host.

In the strict sense neutralization means, inhibiting the binding of specific LPS to its cognate receptor (e.g., Toll-like receptor-4 complex) and hence eliciting biological activity. This neutralization potency is typically determined in a standard assay, e.g. an in vitro or in vivo neutralization assay, e.g. a LAL test, or TLR-4 based assays, where the inhibition of endotoxin's biological activity is measured, e.g. by colorimetry.

Antibodies combating or neutralizing K. pneumoniae are interfering with the pathogens and pathogenic reactions, thus able to limit or prevent infection and/or to ameliorate a disease condition resulting from such infection, or to inhibit K. pneumoniae pathogenesis, in particular dissemination and replication into or within sterile body compartments/sites of the host. In this regard the neutralizing antibody is also understood as being a "protective antibody" meaning that the antibody is responsible for immunity to an infectious agent observed in active or passive immunity. In particular, neutralizing or protective antibodies as described herein are possibly used for therapeutic purposes, e.g. for prophylaxis or therapy, to prevent, ameliorate, treat or at least partially arrest disease symptoms, side effects or progression of disease induced by a pathogen. Specifically, protective antibodies are able to kill or impede replication of live K. pneumoniae cells by e.g. inducing serum bactericidal or opsonophagocytic activities, or remove whole bacterial cells or the LPS molecules thereof from the sterile body sites following therapeutic applications (i.e. given on an established infection). Alternatively, prophylactically applied protective antibodies inhibit establishment of an infection (i.e. spread of *K. pneumoniae* from non-sterile sites to sterile body compartments) by one of the abovementioned or other mechanisms.

The term "biological sample" as used herein shall refer to any material obtained from a subject, such as a human being, that contains, or potentially contains, biological material which could contain *K. pneumoniae*. The biological sample can be a tissue, fluid or cell culture sample. Examples of samples for use in accordance with the invention include, but are not limited to patient samples, e.g., tissue or body fluids, specifically a respiratory tract specimen such as endotracheal aspirates, pleural fluid, lung tap, nasal swab or sputum, a blood sample, stool sample, skin and urine sample or cerebrospinal fluid.

The biological sample typically comprises a complex biological matrix such as complex viscous biological fluids containing multiple types of biological and small organic molecules, for example mucous exudates rich in protein matter. Suitable additives or extraction procedures may be used to reduce the non-specific binding that can be associated with a matrix in the sample and/or lower the matrix viscosity by solubilizing and/or breaking down viscous or solid components of the sample matrix. Sample preparation methods may be employed that liberate markers from organisms and/or break down and/or liquefy biological matrices. Biological matrices that may be analyzed include mucus-containing samples such as nasal secretions, sputum, phlegm, pharyngeal exudates, urethral or vaginal secretions, and washes of such membrane surfaces.

Suitable sample preparation methods include method steps to reduce the effect of the biological matrix on the assay. Such method steps may include but are not limited to, e.g., capture, chromatography, spin-centrifugation and dialysis.

The material obtained from a subject may also be in the form of bacterial isolates, e.g., in the form of a cell culture for cultivating the isolated *K. pneumoniae* or a cell culture product. Culture media may be selective to enrich solely the *K. pneumoniae* population, or non-selective.

Bacterial isolate preparation typically involves an incubating step to maintain the sample in conditions that enhance the proliferation of *K. pneumoniae*, thereby enriching the *K. pneumoniae* population in the sample.

Once the isolate is obtained, the bacterium may be further investigated by biochemical and/or serological tests, e.g., to determine the O type, and the level of gal-III expressed. Several typing methods are available to study *K. pneumoniae* strains. These methods typically include serotyping, standard typing for genetic relationship/phylogeny including multi-locus sequence typing (MLST), or Pulsed Field Gel Electrophoresis (PFGE).

The term "galactan-III" also referred to as "gal-III" as used herein shall refer to the carbohydrate structure of the LPS O-antigen of *K. pneumoniae* comprising a galactose polymer and a structure comprising at least one of the repeating unit of Formula (I). Such repeating unit includes a branched galactose polymer, see FIG. 5. The structure is similar, but distinct from that of the gal-I antigen. Gal-III is herein understood as a new serotype determinant, which is similar, but distinct from the O2a serotype that is characterized by the presence of the gal-I antigen and the absence of the gal-III structure.

The respective O-antigen comprising the gal-III structure is herein referred to as "gal-III antigen" which includes the "gal-III epitope" being recognized by a gal-III specific antibody of the invention. The gal-III antigen is understood as the outer part of the LPS of *K. pneumoniae* of the gal-III O-type, which is the surface accessible antigenic carbohydrate structure comprising one or more specific gal-III epitopes incorporated therein.

Figure 4B:
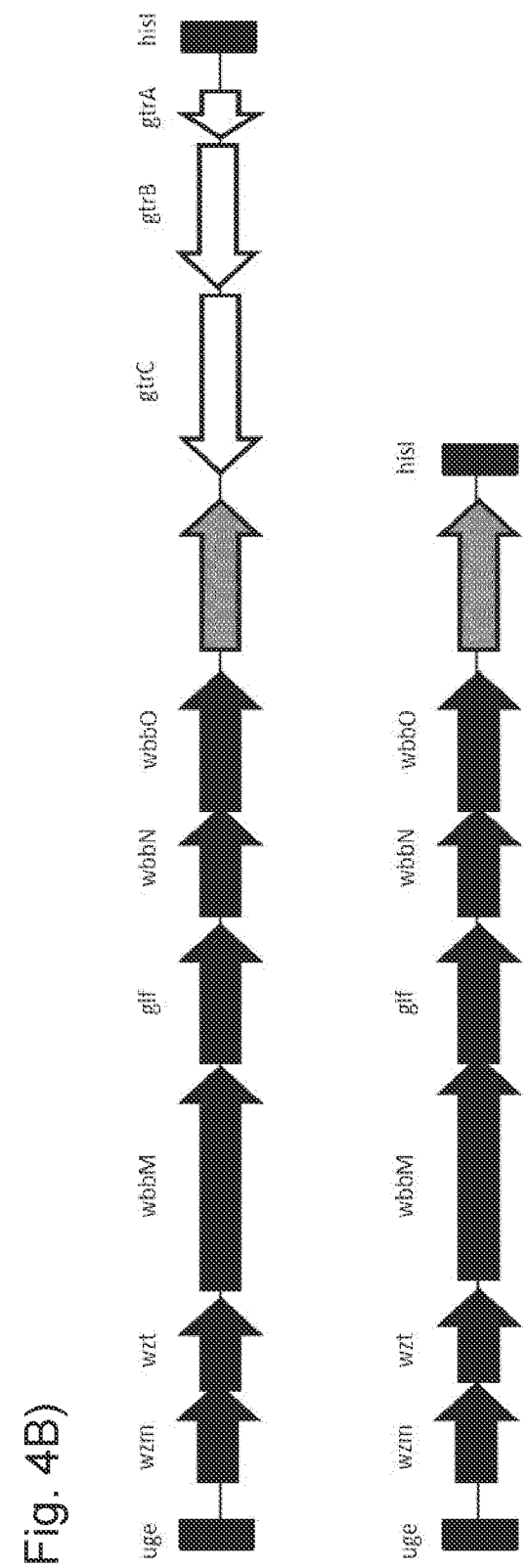

The genotype of *K. pneumoniae* of the gal-III O-type is specifically characterized by the $rfb_{gal-I}$ locus complemented by gtr genes (FIG. 4B), i.e a rfb locus which is extended by additional gtr genes, which is responsible for expressing the branched trigalactose repeat unit that is different from the linear one of the gal-I type.

Any *K. pneumoniae* which is characterized by a LPS O-antigen comprising at least one gal-III structure is herein referred to as *K. pneumoniae* of the gal-III O-type. LPS of *K. pneumoniae* of the gal-III O-type may comprise exclusively the gal-III structure, or both, gal-III and gal-I structures.

The term "galactan-I" also referred to as "gal-I" as used herein shall refer to the carbohydrate structure of the LPS O-antigen of *K. pneumoniae* comprising a galactose polymer and a structure comprising at least one of the repeating unit of Formula (II), but not a repeating unit of Formula (I). Such repeating unit includes a linear galactose polymer. Gal-I is characteristic for the O2a serotype which does not comprise any gal-III antigen.

The respective O-antigen comprising the gal-I structure is herein referred to as "gal-I antigen" which includes the "gal-I epitope" being recognized by a gal-I specific antibody of the invention. The genotype of *K. pneumoniae* of the gal-I O-type is specifically characterized by the $rfb_{gal-I}$ locus which does not incorporate the gtr genes, which is responsible for expressing the linear tri-galactose repeat unit that is different from the branched one of the gal-III type.

The gal-I antigen is understood as the outer part of the LPS of *K. pneumoniae* of the gal-I O-type, which is the surface accessible antigenic carbohydrate structure comprising one or more specific gal-I epitopes incorporated therein, and which does not include any gal-III structure.

"Specific" binding, recognizing or targeting as used herein, means that the binder, e.g., antibody or antigen-binding portion thereof, exhibits appreciable affinity for the target antigen or a respective epitope in a heterogeneous population of molecules. Thus, under designated conditions (e.g., immunoassay), a binder specifically binds to the target gal-III antigen and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different (understood as at least 1 log difference), preferably the difference is at least 100-fold (understood as at least 2 logs difference), and more preferred a least 1000-fold (understood as at least 3 logs difference) as compared to another target.

The term "specificity" is also understood to apply to binders which bind to one or more molecules, e.g. cross-specific binders. Preferred cross-specific (also called poly-specific or cross-reactive) binders targeting at least two different targets or epitopes or nucleotide sequences of such targets or targeting a cross-reactive epitope or nucleotide sequence on at least two different targets, specifically bind the targets with substantially similar binding affinity, e.g. with less than 100-fold difference or even less than 10-fold difference, or, with substantially different binding affinity, e.g. with at least 10 fold or at least 100 fold difference. The cross-specific binder which recognizes both, a first (e.g. gal-III) and a second (e.g. the gal-I) target, which preferentially binds the first target over the second target is typically characterized by equal affinities or a higher affinity to the first target relative to the second one, specifically wherein the differential binding affinity to preferentially bind the first antigen relative to the second antigen is specifically at least equal or more than equal, e.g. at least 1.5 fold, or at least 2-fold, or at least 3-fold, or at least 4-fold, or at least 5 fold, or at least 6-fold, or at least 7-fold, or at least 8-fold, or at least 9-fold, or at least 10-fold higher. Such differential binding may be determined by an immunoassay, preferably immunoblotting, ELISA or other immunological methods.

Preferred antibodies of the invention are binding the gal-III antigen (only gal-III, or preferentially binding gal-III relative to the gal-I antigen), with a high affinity, in particular with a high on and/or a low off rate, or a high avidity of binding. The binding affinity of an antibody is usually characterized in terms of the concentration of the antibody, at which half of the antigen binding sites are occupied, known as the dissociation constant (Kd, or $K_D$). Usually a binder is considered a high affinity binder with a Kd<$10^{-7}$ M, in some cases, e.g. for therapeutic purposes with higher affinities, e.g. with a Kd<$10^{-8}$ M, preferably a Kd<$10^{-9}$ M, even more preferred is a Kd<$10^{-10}$ M.

Yet, in a particularly preferred embodiment the individual antigen binding affinities are of medium affinity, e.g. with a Kd of less than $10^{-6}$ and up to $10^{-8}$ M, e.g. when binding to at least two antigens.

Medium affinity binders may be provided according to the invention, preferably in conjunction with an affinity maturation process, if necessary.

Affinity maturation is the process by which antibodies with increased affinity for a target antigen are produced. Any one or more methods of preparing and/or using affinity maturation libraries available in the art may be employed in order to generate affinity matured antibodies in accordance with various embodiments of the invention disclosed herein. Exemplary such affinity maturation methods and uses, such as random mutagenesis, bacterial mutator strains passaging, site-directed mutagenesis, mutational hotspots targeting, parsimonious mutagenesis, antibody shuffling, light chain shuffling, heavy chain shuffling, CDR1 and/or CDR1 mutagenesis, and methods of producing and using affinity maturation libraries amenable to implementing methods and uses in accordance with various embodiments of the invention disclosed herein, include, for example, those disclosed in: Prassler et al. (2009); Immunotherapy, Vol. 1(4), pp. 571-583; Sheedy et al. (2007), Biotechnol. Adv., Vol. 25(4), pp. 333-352; WO2012/009568; WO2009/036379; WO2010/105256; US2002/0177170; WO2003/074679.

With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody according to the invention exhibits at least a 2 fold increase in affinity of binding, preferably at least a 5, preferably at least 10, preferably at least 50, or preferably at least 100 fold increase. The affinity maturation may be employed in the course of the selection campaigns employing respective libraries of parent molecules, either with antibodies having medium binding affinity to obtain the antibody of the invention having the specific target binding property of a binding affinity Kd<$10^{-8}$ M. Alternatively, the affinity may be even more increased by affinity maturation of the antibody according to the invention to obtain the high values corresponding to a Kd of less than $10^{-9}$ M, preferably less than $10^{-10}$ M or even less than $10^{-11}$ M, most preferred in the picomolar range.

In certain embodiments binding affinity is determined by an affinity ELISA assay. In certain embodiments binding affinity is determined by a BIAcore, ForteBio or MSD assays. In certain embodiments binding affinity is determined by a kinetic method. In certain embodiments binding affinity is determined by an equilibrium/solution method.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays, e.g. as described in Harlow, et al., ANTIBODIES: A LABORATORY MANUAL, Cold Spring Harbor Laboratory Press, Cold Spring Harbor, N.Y., 1988).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "compete" with each other for binding of their respective epitope(s). Antibodies that compete with any of the exemplified antibodies for binding the gal-III antigen are particularly encompassed by the present invention.

Competition herein means a greater relative inhibition than about 30% as determined by competition ELISA analysis or by ForteBio analysis. It may be desirable to set a higher threshold of relative inhibition as criteria of what is a suitable level of competition in a particular context, e.g., where the competition analysis is used to select or screen for new antibodies designed with the intended function of the binding of the antigen. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

The term "diagnostic kit" as used herein refers to a kit or set of parts, which in combination or mixture can be used to carry out the measurement/detection of one or more analytes or markers to determine a disease or disease condition, or to predict the disease or the disease progression. In particular, the kit contains at least a detection molecule and/or a binder, wherein the detection molecule and/or the binder specifically recognizes the analyte or marker, or a reaction product of such analyte or marker. In addition, various reagents or tools may be included in the kit. The diagnostic kit may comprise any useful reagents for carrying out the subject methods, including substrates such as microbeads or planar arrays or wells, reagents for biomarker isolation, detection molecules directed to specific targets, reagents such as primers for nucleic acid sequencing or amplification, arrays for nucleic acid hybridization, detectable labels, solvents or buffers and the like, various linkers, various assay components, blockers, and the like.

A kit may also include instructions for use in a diagnostic method. Such instructions can be, for example, provided on a device included in the kit, e.g. tools or a device to prepare a biological sample for diagnostic purposes, such as separating a cell and/or protein containing fraction before determining a marker. The kit may conveniently be provided in the storage stable form, such as a commercial kit with a shelf-life of at least 6 months.

Specific diagnostic kits also comprise a solid support comprising a detection molecule or having an immobilized patterned array of detection molecules directed against markers of interest, preferably including a first region containing a first binding reagent directed against a first marker and a second region containing a second binding reagent directed against a second marker.

In particular, a sandwich format can be used. For example, one or more binder is conjugated to a substrate prior to the contacting with a biological sample. The one or more binder may be conjugated to a detectable label to serve as a detection molecule. In other embodiments, the one or more binder is conjugated to a detectable label. In this configuration, the one or more binders may be conjugated to a substrate prior to the contacting with the biological sample to serve as a capture agent. Furthermore, the one or more binder can be conjugated to a substrate prior to the contacting with the biological sample, and/or the one or more binder is conjugated to a detectable label. In such cases, the one or more binder can act as either or both of a capture agent and a detection agent.

The diagnostic kit is specifically provided for use in an immunoassay, wherein the detection molecule is a specific binder that binds to the analyte or marker by an immunoreaction. Such binder may be antibodies or antibody fragments or antibody-like scaffolds binding to a target antigen.

Suitable immunoassays are any of ELISA, CIA, RIA, IRMA, agglutination assay, immunochromatography, dip-stick assay and Western-blot.

The term "*K. pneumoniae* infection" and "*K. pneumoniae* colonization" is understood in the following way: *Klebsiella pneumoniae* is a Gram-negative bacterium that is a member of the family Enterobacteriaceae. It is a ubiquitous bacterium, which can also colonize the human host, typically in the intestines or the upper airways. Being an opportunistic pathogen, from these sites it can invade sterile body sites in case not properly controlled by the immune system. Uncontrolled bacterial replication at these otherwise sterile sites will induce inflammation, in a great part, mediated by the endotoxin (i.e. LPS) molecules released from *K. pneumoniae*. In case of bacteremia, endotoxin molecules may trigger septic shock.

*K. pneumoniae* colonization means that the subject has a sufficiently high concentration of *K. pneumoniae* bacteria at a site that they can be detected, yet the bacteria are causing no signs or symptoms. Colonization can persist for a long period of time, with resolution influenced by the immune response to the organism, competition at the site from other organisms and, sometimes, use of antimicrobials.

In general, bacteremias caused by *K. pneumoniae* may be successfully treated with known conventional antibacterial therapy, such as treatment with antibiotics, steroid and non-steroid inhibitors of inflammation. The present invention provides for a new immunotherapy, employing antibodies specifically recognizing *K. pneumoniae*, which is optionally combined with anti-bacterial or anti-inflammatory therapy. Exemplary antibiotics used for treating patients with *K. pneumoniae* infection are aminoglycosides, cephalosporines, aminopenicillines, carbapenems, fluoroquinolons, tygecycline, colistin, etc.

Multi-drug resistant (MDR) *K. pneumoniae* is particularly understood as those strains demonstrating resistance to three or more classes of antibiotics, e.g. the following agents/groups: penicillins, cephalosporins, carbapenems, aminoglycosides, tetracyclines, fluoroquinolones, nitrofurantoin, trimethoprim (and its combinations), fosfomycin, polymixins, chloramphenicol, azthreonam, or tigecycline.

With the recent emergence of antibiotic-resistant strains, treating bacteremias of this nature has become significantly more difficult. Patients who develop MDR *K. pneumoniae* disease have longer hospital and ICU stays, high mortality, and greater health care costs than patients without *K. pneumoniae* disease. Patient care may be improved and nosocomial infections may be reduced by preventing, rather than treating, *K. pneumoniae* disease prophylaxis when a patient is heavily colonized by MDR *K. pneumoniae*.

*K. pneumoniae* disease is specifically understood as a disease caused by *K. pneumoniae* infection. Such diseases include local and systemic disease. Severe cases of disease are e.g. primary and secondary bacteremia, pneumonia, urinary tract infection, liver abscess, peritonitis, or meningitis.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library or library of antigen-binding sequences of an antibody, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

Selective binding can be further improved by recombinant antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

The term "subject" as used herein shall refer to a warm-blooded mammalian, particularly a human being or a non-human animal. *K. pneumoniae* is a critically important human pathogen that is also an emerging concern in veterinary medicine. It is present in a wide range of non-human animal species. Thus, the term "subject" may also particularly refer to animals including dogs, cats, rabbits, horses, cattle, pigs and poultry. In particular the medical use of the invention or the respective method of treatment applies to a subject in need of prophylaxis or treatment of a disease condition associated with a *K. pneumoniae* infection. The subject may be a patient at risk of a *K. pneumoniae* infection or suffering from disease, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of *K. pneumoniae* disease conditions. In particular, the subject is treated, which is either at risk of infection or developing such disease or disease recurrence, or a subject that is suffering from such infection and/or disease associated with such infection.

Specifically the term "prophylaxis" refers to preventive measures which is intended to encompass prevention of the onset of pathogenesis or prophylactic measures to reduce the risk of pathogenesis.

Specifically, the treatment may be by interfering with the pathogenesis of *K. pneumoniae* as causal agent of the condition, The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g. chromatographic methods, polyacrylamide gel electrophoresis, HPLC analysis, and the like).

The term "therapeutically effective amount", used herein interchangeably with any of the terms "effective amount" or "sufficient amount" of a compound, e.g. an antibody of the present invention, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of *K. pneumoniae* pathogenesis, for example, adhesion and colonization of mucosal surfaces, uncontrolled replication within sterile body sites, and toxicity of host cells by bacterial products.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A therapeutically effective amount of the antibody as described herein, such as provided to a human patient in need thereof, may specifically be in the range of 0.5-50 mg/kg, preferably 5-40 mg/kg, even more preferred up to 20 mg/kg, up to 10 mg/kg, up to 5 mg/kg, though higher doses may be indicated e.g. for treating acute disease conditions. The dose can be much lower if a highly potent antibody is used. In such case, the effective amount may be in the range of 0.005 to 5 mg/kg, preferably 0.05 to 1 mg/kg.

Moreover, a treatment or prevention regime of a subject with a therapeutically effective amount of the antibody of the present invention may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

Monoclonal antibodies (mAbs) highly specific to gal-III have great potential as diagnostic reagents for the identification of MDR *Klebsiella pneumoniae*, specifically MDR strains belonging to the ST258 lineage. Furthermore, in particular when humanized, these mAbs are suitable to be used for the prophylaxis (e.g. for high risk groups) and treatment of *K. pneumoniae* infections caused by ST258-gal-III strains.

The gal-III and gal-I carbohydrate structures were thought to be very similar and no different antigens. The genetic background of O-antigen synthesis in MDR *Klebsiella pneumoniae*, ST258 strains was not fully elucidated. It was surprising that a specific gene adjacent to the rfb (wb) cluster (encoding glycosyltransferases, gtr-s) forms the basis of PCR based identification of strains of the gal-III O-type.

There is evidence of heterogeneity within the rfb gene clusters encoding the O-antigen factor galactan-I. The size difference observed between the variants originates from the presence or absence of a ~3-kb fragment carrying gtr (glycosyltransferase)-like genes. A PCR reaction developed to differentiate between the variants revealed that more than 50% of all O1 and O2 *Klebsiella* clinical isolates and over 80% of all ST258 strains carry the gtr-like locus.

It was surprising that an antibody of invention could specifically bind the gal-III antigen. It turned out that immunization of mice with a gtr+ O2 strain elicits antigalactan antibodies, which exclusively recognize galactan-I molecules decorated by the gtr locus (i.e. galactan-III antigens). Though the nature of this modification was identified as the same branching galactan structure described earlier as the repeating unit of serotype O2 (2a, 2f, 2g), the structures were not found to be antigenically different. The present invention provides for the first time mAbs specific to galactan-III generated by standard hybridoma technique. Capacity of this mAbs to bind to the surface of live O2 gtr+ *Klebsiella* isolates (including ST258 strains) was observed. It was surprising that protective efficacy of galactan-III specific mAbs could be shown in murine models of bacteraemia and endotoxaemia. The putative mode of action for protection is neutralization of endotoxin, which was confirmed by an in vitro functional assay.

Aiming to develop therapeutic monoclonal antibodies for the prevention and treatment of infections caused by MDR *Klebsiella* strains, the molecular target of specific mAbs suitably is the LPS O-antigen, which shows limited heterogeneity in *Klebsiella*. Such O-side chain is considered immunorelevant because not fully masked by bulky capsular polysaccharide.

Once antibodies with the desired binding properties are identified, such antibodies, including antibody fragments can be produced by methods well-known in the art, including, for example, hybridoma techniques or recombinant DNA technology.

Recombinant monoclonal antibodies can, for example, be produced by isolating the DNA encoding the required antibody chains and transfecting a recombinant host cell with the coding sequences for expression, using well known recombinant expression vectors, e.g. the plasmids of the invention or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to humanize the antibody or to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the gal-III target and greater efficacy against *Klebsiella pneumoniae*, specifically the MDR clone ST258. It will be apparent to one of skill in the art that one or more polynucleotide changes can be made to the antibody and still maintain its binding ability to the target gal-III antigen.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2):191-202) and Lee and Kwak (2003, J. Biotechnology 101:189-198) describe the production of monoclonal antibodies from separately produced heavy and light chains, using plasmids expressed in separate cultures of host cells. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

If desired, the antibody of the invention, e.g. any of the antibodies of FIG. 1 or FIG. 2, may be sequenced and the polynucleotide sequence may then be cloned into a vector for expression or propagation. The sequence encoding the antibody may be maintained in vector in a host cell and the host cell can then be expanded and frozen for future use. Production of recombinant monoclonal antibodies in cell culture can be carried out through cloning of antibody genes from B cells by means known in the art.

In another aspect, the invention provides an isolated nucleic acid comprising a sequence that codes for production of the recombinant antibody of the present invention.

An antibody encoding nucleic acid can have any suitable characteristics and comprise any suitable features or combinations thereof. Thus, for example, an antibody encoding nucleic acid may be in the form of DNA, RNA, or a hybrid thereof, and may include non-naturally-occurring bases, a modified backbone, e.g., a phosphorothioate backbone that promotes stability of the nucleic acid, or both. The nucleic acid advantageously may be incorporated in an expression cassette, vector or plasmid of the invention, comprising features that promote desired expression, replication, and/or selection in target host cell(s). Examples of such features include an origin of replication component, a selection gene component, a promoter component, an enhancer element component, a polyadenylation sequence component, a termination component, and the like, numerous suitable examples of which are known.

The present disclosure further provides the recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

Monoclonal antibodies are produced using any method that produces antibody molecules by cell lines in culture, e.g. cultivating recombinant eukaryotic (mammalian or insect) or prokaryotic (bacterial) host cells. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

Antibodies of the present invention may be identified or obtained employing a hybridoma method. In such method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

mAbs may then be purified from hybridoma supernatants for further testing for its specific binding of the gal-III antigen and possibly for its differential binding affinity to preferentially bind the gal-III antigen relative to the gal-I antigen, and engineering of antibodies, e.g. for different diagnostic or therapeutic purposes.

Gal-III specific antibodies, in some instances, emerge through screening against the single gal-III antigen. To increase the likelihood of isolating differentially binding clones one would apply multiple selective pressures by processively screening against the different antigens. Special mAb selection strategies employ the gal-III and gal-I components or other *K. pneumoniae* antigens in an alternating fashion.

Screening methods for identifying antibodies with the desired selective binding properties may be done by display technologies using a library displaying antibody sequences or antigen-binding sequences thereof (e.g. using phage, bacterial, yeast or mammalian cells; or in vitro display systems translating nucleic acid information into respective (poly)peptides). Reactivity can be assessed based on ELISA, Western blotting or surface staining with flow cytometry, e.g. using standard assays.

Isolated antigen(s) may e.g. be used for selecting antibodies from an antibody library, e.g. a yeast-displayed antibody library.

For example, the invention specifically provides for gal-III specific antibodies, which are obtained by a process to identify antibodies with specificities to bind the gal-III antigen, e.g. by a specific discovery selection scheme. Accordingly, an antibody library including antibodies showing reactivity with the gal-III target, may be selected for reactivity with the target.

The invention moreover provides pharmaceutical compositions which comprise an antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination provided by the invention. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an antibody of the present invention and one or more therapeutically active agents are formulated. Stable formulations of the antibody of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an antibody of the present invention, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, e.g. employing inhalable technology or pulmonary delivery systems, vaginally, parenterally, rectally, or intraocularly.

Examplary formulations as used for parenteral administration include those suitable for subcutaneous, intramuscular or intravenous injection as, for example, a sterile solution, emulsion or suspension.

In one embodiment, the antibody of the present invention is the only therapeutically active agent administered to a subject, e.g. as a disease modifying or preventing monotherapy.

In another embodiment, the antibody of the present invention is combined with further antibodies in a cocktail, e.g. combined in a mixture or kit of parts, to target Klebsiella pneumoniae, specifically MDR strains belonging to the ST258 lineage, such that the cocktail contains more than one therapeutically active agents administered to a subject, e.g. as a disease modifying or preventing combination therapy.

Further, the antibody of the present invention may be administered in combination with one or more other therapeutic or prophylactic agents, including but not limited to standard treatment, e.g. antibiotics, steroid and non-steroid inhibitors of inflammation, and/or other antibody based therapy, e.g. employing anti-bacterial or anti-inflammatory agents.

A combination therapy is particularly employing a standard regimen, e.g. as used for treating infection by Klebsiella pneumoniae, specifically the MDR clone ST258. This may include antibiotics, e.g., tygecycline, colistin, polymixin B, and beta lactams combined with non-beta lactam inhibitors.

In a combination therapy, the antibody may be administered as a mixture, or concomitantly with one or more other therapeutic regimens, e.g. either before, simultaneously or after concomitant therapy.

The biological properties of the antibody or the respective pharmaceutical preparations of the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic or as a prophylactic with the appropriate half-life, effector function, (cross-) neutralizing activity and/or immune response upon active or passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody and respective pharmaceutical compositions of the present invention may be tested in humans to determine their therapeutic or prophylactic efficacy, toxicity, immunogenicity, pharmacokinetics, and/or other clinical properties.

The subject matter of the following definitions is considered embodiments of the present invention:

1. An isolated antibody that specifically recognizes a galactan-III epitope of the lipopolysaccharide (LPS) O-antigen structure of *Klebsiella pneumoniae*, which epitope is incorporated in galactan-III repeating units, wherein the galactan-III repeating unit is a branched galactose homopolymer of Formula (I)

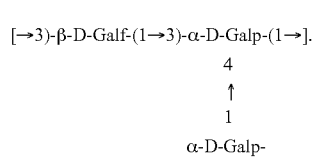

Formula (I)

2. The antibody of definition 1, which preferentially binds to the galactan-III epitope relative to the galactan-I epitope, or which does not cross-react with the galactan-I epitope, wherein the galactan-I epitope is incorporated in galactan-I repeating units of the LPS O2a-antigen structure of *Klebsiella pneumoniae*, and wherein the galactan-I repeating unit is a linear galactose homopolymer of Formula (II)

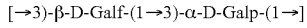

Formula (II)

3. The antibody of definition 1 or 2, wherein the galactan-III epitope is of multi-drug resistant (MDR) *Klebsiella pneumoniae*, specifically the MDR clone ST258.

4. The antibody of any of definitions 1 to 3, which has an affinity to bind the galactan-III epitope with a Kd of less than $10^{-7}$M, preferably less than $10^{-8}$M, even more preferably less than $10^{-9}$M.

5. The antibody of any of definitions 1 to 4, which is neutralizing endotoxin of *Klebsiella pneumoniae* strains expressing the galactan-III epitope.

6. The antibody of any of definitions 1 to 5, which is neutralizing endotoxin of *Klebsiella pneumoniae* strains expressing the galactan-III epitope, wherein the neutralization potency is at least the potency of a reference antibody, which comprises
   a) a CDR1 consisting of the amino acid sequence of SEQ ID 10; and
   b) a CDR2 consisting of the amino acid sequence of SEQ ID 11; and
   c) a CDR3 consisting of the amino acid sequence of SEQ ID 12; and
   d) a CDR4 consisting of the amino acid sequence of SEQ ID 19; and
   e) a CDR5 consisting of the amino acid sequence of SEQ ID 17; and
   f) a CDR6 consisting of the amino acid sequence of SEQ ID 18, according to the nomenclature of Kabat.

7. The antibody of definition 5 or 6, wherein the strain is characterized by a rfb$_{gal-I}$ locus incorporating gtr genes.

8. The antibody of any of definitions 5 to 7, which recognizes the MDR *Klebsiella pneumoniae* clone ST258.

9. The antibody of any of definitions 1 to 8, which is a full-length monoclonal antibody, an antibody fragment thereof comprising at least one antibody domain incorporating the binding site, or a fusion protein comprising at least one antibody domain incorporating the binding site, specifically wherein the antibody is a non-naturally occurring antibody which comprises a randomized or artificial amino acid sequence.

10. The antibody of any of definitions 1 to 9, which is of human, humanized, chimeric, or murine origin.

11. The antibody of any of definitions 1 to 10, which is a monoclonal antibody.

12. The antibody of any of definitions 1 to 11, which comprises at least an antibody heavy chain variable region (VH), which is characterized by any of the CDR1 to CDR3 sequences as listed in Table 1, which are designated according to the numbering system of Kabat, or functionally active CDR variants thereof.

13. The antibody of definition 12, which is
A)
selected from the group consisting of group members i) to iv), wherein
   i)
   is an antibody which comprises
      a) a CDR1 consisting of the amino acid sequence of SEQ ID 1; and
      b) a CDR2 consisting of the amino acid sequence of SEQ ID 2; and
      c) a CDR3 consisting of the amino acid sequence of SEQ ID 3;
   ii)
   is an antibody which comprises
      a) a CDR1 consisting of the amino acid sequence of SEQ ID 4; and
      b) a CDR2 consisting of the amino acid sequence of SEQ ID 5; and
      c) a CDR3 consisting of the amino acid sequence of SEQ ID 6;
   iii)
   is an antibody which comprises
      a) a CDR1 consisting of the amino acid sequence of SEQ ID 7; and
      b) a CDR2 consisting of the amino acid sequence of SEQ ID 8; and
      c) a CDR3 consisting of the amino acid sequence of SEQ ID 9;
   iv)
   is an antibody which comprises
      a) a CDR1 consisting of the amino acid sequence of SEQ ID 10; and
      b) a CDR2 consisting of the amino acid sequence of SEQ ID 11; and
      c) a CDR3 consisting of the amino acid sequence of SEQ ID 12;
or
B) an antibody which is a functionally active variant of a parent antibody that is any of the group members of A, which comprises at least one functionally active CDR variant of any of the CDR1, CDR2 or CDR3 of the parent antibody.

14. The antibody of definition 12 or 13, comprising a VH amino acid sequence selected from any of the VH sequences as depicted in FIG. 2.

15. The antibody of any of definitions 12 to 14, which further comprises an antibody light chain variable region (VL), which comprises any of the CDR4 to CDR6 sequences as listed in Table 1, which are designated according to the numbering system of Kabat, or functionally active CDR variants thereof.

16. The antibody of definition 15, which is
A) selected from the group consisting of group members i) to iv), wherein
i) is an antibody which comprises
a) a CDR4 consisting of the amino acid sequence of SEQ ID 13; and
b) a CDR5 consisting of the amino acid sequence of SEQ ID 14; and
c) a CDR6 consisting of the amino acid sequence of SEQ ID 15;
ii) is an antibody which comprises
a) a CDR4 consisting of the amino acid sequence of SEQ ID 16; and
b) a CDR5 consisting of the amino acid sequence of SEQ ID 17; and
c) a CDR6 consisting of the amino acid sequence of SEQ ID 18;
iii) is an antibody which comprises
a) a CDR4 consisting of the amino acid sequence of SEQ ID 19; and
b) a CDR5 consisting of the amino acid sequence of SEQ ID 20; and
c) a CDR6 consisting of the amino acid sequence of SEQ ID 18;
iv) is an antibody which comprises
a) a CDR4 consisting of the amino acid sequence of SEQ ID 19; and
b) a CDR5 consisting of the amino acid sequence of SEQ ID 17; and
c) a CDR6 consisting of the amino acid sequence of SEQ ID 18;
or
B) an antibody which is a functionally active variant of a parent antibody that is any of the group members of A, which comprises at least one functionally active CDR variant of any of the CDR4, CDR5 or CDR6 of the parent antibody.

17. The antibody of definition 16, comprising a VL amino acid sequence selected from any of the VL sequences as depicted in FIG. 2.

18. The antibody of any of definitions 12 to 17, which comprises
a) the CDR1-CDR6 sequences of any of the antibodies as listed in Table 1; or
b) the VH and VL sequences of any of the antibodies as depicted in FIG. 2; or
c) which is a functionally active variant of a parent antibody that is characterized by the sequences of a)-c), preferably wherein
i. the functionally active variant comprises at least one functionally active CDR variant of any of the CDR1-CDR6 of the parent antibody; and/or
ii. the functionally active variant comprises at least one point mutation in the framework region of any of the VH and VL sequences; and further wherein
iii. the functionally active variant has a specificity to bind the same epitope as the parent antibody; and/or
iv. the functionally active variant is a human, humanized, chimeric or murine and/or affinity matured variant of the parent antibody.

19. The antibody of any of definitions 1 to 18, comprising a functionally active CDR variant of any of the CDR sequences as listed in Table 1, wherein the functionally active CDR variant comprises at least one of
a) 1, 2, or 3 point mutations in the parent CDR sequence; and/or
b) 1 or 2 point mutations in any of the four C-terminal or four N-terminal, or four centric amino acid positions of the parent CDR sequence; and/or
c) at least 60% sequence identity with the parent CDR sequence; preferably wherein the functionally active CDR variant comprises 1 or 2 point mutations in any CDR sequence consisting of less than 4 or 5 amino acids.

20. The antibody of any of definitions 1 to 19, for use in treating a subject at risk of or suffering from *Klebsiella pneumoniae* infection or colonization comprising administering to the subject an effective amount of the antibody to limit the infection in the subject or to ameliorate a disease condition resulting from said infection, preferably for treatment or prophylaxis of any of primary and secondary bacteremia, pneumonia, urinary tract infection, liver abscess, peritonitis, or meningitis.

21. A pharmaceutical preparation comprising the antibody of any of definitions 1 to 19, preferably comprising a parenteral or mucosal formulation, optionally containing a pharmaceutically acceptable carrier or excipient.

22. Use of the antibody of any of definitions 1 to 19, for diagnosis of *Klebsiella pneumoniae* infection or colonization, or an associated disease such as primary and secondary bacteremia, pneumonia, urinary tract infection, liver abscess, peritonitis, or meningitis in a subject.

23. Use according to definition 22, wherein the subject is an immunocompromised or immunosuppressed patient, or a contact thereof.

24. Diagnostic preparation of the antibody of any of definitions 1 to 19, comprising the antibody and a further diagnostic reagent in a composition or a kit of parts, comprising the components
a) the antibody; and
b) the further diagnostic reagent;
c) and optionally a solid phase to immobilize at least one of the antibody and the diagnostic reagent.

25. Diagnostic preparation of definition 24, wherein the further diagnostic reagent is a diagnostic label or a reagent specifically reacting with the antibody and/or the reaction product of the antibody binding to its antigen.

26. Method of diagnosing *Klebsiella pneumoniae* infection or colonization in a subject caused by a *Klebsiella pneumoniae* strain, comprising
a) providing an antibody according to any of definitions 1 to 19, and
b) detecting if the antibody specifically immunoreacts with the galactan-III epitope in a biological sample of the subject to be tested, thereby diagnosing *Klebsiella pneumoniae* infection or colonization.

27. Method of definition 26, wherein the biological samples is a body fluid or tissue sample, preferably a sample selected from the group consisting of a blood sample, stool sample, skin sample, urine sample, cerebrospinal fluid, and a respiratory tract specimen such as endotracheal aspirates, pleural fluid, lung tap, nasal swab or sputum, or a *Klebsiella pneumoniae* isolate originating from any of the foregoing.

28. Isolated nucleic acid encoding an antibody of any of the definitions 1 to 19.

29. An expression cassette or a plasmid comprising a coding sequence to express a proteinaceous construct or a protein, which comprises a VH and/or VL of an antibody of any of definitions 1 to 19.

30. A host cell comprising an expression cassette or a plasmid of definition 29.

31. Method of producing an antibody of any of definitions 1 to 19, wherein a host cell of definition 30 is cultivated or maintained under conditions to produce said antibody.

32. A method of identifying a candidate antibody comprising:
   a) providing a sample containing an antibody or antibody-producing cell; and
   b) assessing for binding of an antibody in or produced by the sample with a galactan-III epitope as defined in definition 1, wherein a positive reaction between the antibody and the epitope identifies the antibody as candidate antibody.

33. A method of identifying a candidate antibody comprising:
   a) providing a sample containing an antibody or antibody-producing cell; and
   b) assessing for binding of an antibody in or produced by the sample with the galactan-III epitope as defined in definition 1, wherein a specific positive reaction between the antibody and the galactan-III epitope relative to the galactan-I epitope identifies the antibody as candidate antibody.

34. A method of producing an antibody of any of definitions 1 to 19, comprising
   a) providing a candidate antibody identified according to definition 32 or 33; and
   b) producing a monoclonal antibody, or a humanized or human form of the candidate antibody, or a derivative thereof with the same epitope binding specificity as the candidate antibody.

The present invention is further illustrated by the following examples without being limited thereto.

EXAMPLES

Example 1: Identification of the Genetic Background of a Novel Galactan Structure Since the original description (3) of the galactan-I specific rfb (also known as wb) cluster several full genome sequences have become available. As the rfb cluster always integrates between two conserved genes (uge and hisI), the exact size of the rfb loci could be determined. In silico analysis revealed two alternative lengths of the rfb operon (FIG. 4A). A detailed analysis of these sequences (FIG. 4B) revealed that there are additional genes within the rfb cluster not identified by Clarke et al (3).

Even the shorter full length rfb operon is approx. 2 kb longer than that described by Clarke et al. and contains an additional gene annotated as hypothetical glycosyltransferase family protein. This gene shows poor homology between the long and short rfb operons. Given that the cloned cluster devoid of this gene restored galactan-I synthesis (5) this gene appears to be dispensable for galactan-I expression.

In the longer form of the rfb locus there is an additional 3 kb region comprising 3 genes organized into one operon on the opposite DNA strand. These genes show high sequence similarity to the glycosyltransferase family often carried by mobile genetic elements in various members of Enterobacteriaceae. This kind of horizontally acquired glycosyltransferases are thought to play a role in serotype-conversion (6) or increase intra- and inter-strain phenotypic diversity. Interestingly, in case of *Klebsiella oxytoca* the identical gtr cluster was found at a chromosomal site unlinked to the rfb cluster (unpublished finding). It is, therefore, possible that certain *K. pneumoniae* strains obtained this cluster by horizontal gene transfer from *K. oxytoca*.

The structure of O-antigen subunits purified from an O2 strain carrying the longer rfb locus (i.e. incorporating the gtr genes) showed a branching tri-galactose repeat unit (FIG. 5) that is different from the galactan-I structure. This structure was identified earlier as a subserotype of O2 termed as O2(2a, 2f, 2g) by Kelly et al. (5). Structural analysis of an O2 strain carrying the short operon on its chromosome trans-complemented with either an empty vector or the gtr genes cloned in the vector proved that addition of the branching galactose at 1-4 linkage is encoded by the gtr genes (see example 3, below).

In contrast to what has been published earlier (5), biochemical analysis showed that this modification of galactan-I repeating units is not fully stoichiometric, although the vast majority of the units are galactan-III. Stoichiometry of the modification, nevertheless, may be strain dependent as well as under the influence of expressional regulation and hence needs further investigation.

Example 2: Epidemiology of Galactan-III

In order to detect the gtr-like genes within the rfb cluster in clinical isolates of *K. pneumoniae*, primers annealing to the conserved wbbO and hisI genes (see FIG. 4B) were designed (Table 2 below).

TABLE 2

Primers used for the detection of gtr+ and gtr- strains

| Primer name | Primer sequence (5'-3') | Melting temperature (° C.) | Fragment size in gtr- operon (bp) | Fragment size in gtr+ operon (bp) |
|---|---|---|---|---|
| wbbO rev | TGTTGTGGAGTAAAGGACTGGGCG, SEQ ID 39 | 65.8 | 2183 | 5020 |
| hisI | ACCGCTTCGAGCTGAAGAATGAG, SEQ ID 40 | 64 | | |

O1, O2 and O2ac prototype strains of *K. pneumoniae* were tested for the presence of the gtr-like genes with the above described primers. Genomic DNA was purified from the strains with Wizard® Genomic DNA purification kit (Promega) according to the manufacturer's instruction. PCR reaction was set up with Phusion® High-Fidelity PCR Master Mix (Thermo) in 20µl mixture with 20 pmol of forward and reverse primers and 0.2 µl purified gDNA. PCR was run in a TProfessional TRIO Thermocycler (Biometra) with the following program:

| | | |
|---|---|---|
| Initial denaturing | 98° C. | 1 min |
| Denaturing | 98° C. | 30 sec |
| Annealing | 64° C. | 30 sec |
| Elongation | 72° C. | 3 min |
| Final elongation | 72° C. | 5 min |
| cycles | | 30 cycles |

Reaction mixture was loaded on 1% agarose gel, visualized with GelRed™ (Biotium) and the image was captured with ImageQuant™ LAS 4000 (GE Healthcare) (FIG. 6).

The PCR confirmed that gtr+ and gtr− isolates can be detected among both O1 and O2 strains. To elucidate the frequency of gtr+ and gtr− isolates among clinical isolates, screened 45 O1 and 47 O2 clinical isolates were screened from different geographical origin. Among the O1 isolates isolated 27 (60%) gtr− and 18 (40%) gtr+ isolates were isolated, among the O2 strains, identified 15 (32%) gtr− and 32 (68%) gtr+ strains were identified.

Interestingly, it was found that that the majority of strains belonging to the multi-drug resistant KPC (Klebsiella pneumoniae carbapenemase)-producing endemic clone ST258 carry the operon encoding galactan-III (i.e. the long $rfb_{gal-I}$ locus incorporating the gtr genes). 27 ST258 isolates were analysed by PCR and additionally 224 genome sequences available in databases were analysed in silico. A total of 210 (83.6%) of these strains carried an intact rfb operon incorporating the gtr genes (i.e. expected to express galactan-III antigen). Genomes of many of the remaining strains contained at least parts of the gtr genes, however, were not expected to express intact galactan-III due to deletions or transposon insertions.

Since the genetic background of galactan-II synthesis was recently described (4), O1 and 2 strains could be differentiated solely by analysis of the genomic sequences. However, none of the ST258 isolates carried these O1 specific determinants. Moreover none of the available ST258 isolates reacted to galactan-II specific mAbs, confirming that these isolates are of the O2 serogroup.

These data suggest that the clonal lineage ST258 is strongly associated with expression of galactan-III O-antigens and apparently, in the majority of ST258 strain galactan-III is the sole O-side chain determinant (i.e. galactan-III antigens are not capped by galactan-II). This renders galactan-III an attractive target for antibodies for immune based diagnostics and/or therapeutics.

Example 3: Generation of Monoclonal Antibodies Specific to Galactan-III

Murine monoclonal mAbs were generated by standard hybridoma technique using mice immunized with gtr+ O2 (i.e. gal-III expressing) strain. Four mAbs were selected that showed specificity to galactan-III antigens. In order to investigate whether binding of these mAbs is influenced by the gtr-mediated decoration of galactan-I molecules, a panel of LPS molecules purified from gtr− as well as gtr+ O1 and O2 strains were investigated by immunoblots. Antibodies were diluted to 1 µg/ml concentration, anti-mouse IgG secondary antibody was diluted in 1:20,000.

All 4 mAbs showed identical binding pattern. The results obtained with one representative mAb (9H9-H7) are shown in FIG. 7. Except for one strain (Kp67, lane 8), all O-antigens obtained from gtr+ strains were stained strongly, while none of the gtr− LPS molecules were recognized by this mAb (nor the other 3). Although strain Kp67 was found to be PCR positive for the gtr-locus, it appears to be phenotypically negative for the putative gtr-mediated modification. The reason for the contradiction most probably originates from mutations within the rfb operon as suggested by the rough LPS phenotype (i.e. by the lack of any detectable O-antigens) on silver stained gels (data not shown).

In order to further confirm specificity of these mAbs, immune reactivity was investigated on a panel of isogenic derivatives (FIG. 8) As expected, lack of binding was observed to LPS extracted from an O2 gtr− strain (FIG. 8 lane 2). Upon complementation with a plasmid carrying the gtr genes strong binding was detected (FIG. 8 lanes 5 and 6).

Example 4: Biolayer Interferometry (BLI) Measurement

Antibody binding characteristics were investigated by biolayer interferometry (BLI). Antibody binding was measured by immobilizing biotinylated D-galactan III polysaccharide antigen (purified from an O2 gtr+ K. pneumoniae strain) on streptavidin sensors (ForteBio, Pall Life Sciences) and monitoring the association of the chimeric mAbs (10 µg/mL) to the preloaded sensors for 10 min in DPBS containing 1% bovine serum albumin (BSA) and 0.05% Tween-20, followed by dissociation (1 hour) in the same buffer. The $K_d$, $k_{on}$ and $k_{off}$ values were determined using the Data Analysis 7 software (ForteBio, Pall Life Sciences). Response values below 0.05 nm were considered negative.

The $K_d$, $k_{on}$ and $k_{off}$ values are summarized in Table 3. All mAbs showed strong avid binding to the purified antigen ($K_d$ 0.1 nM-10 nM), with similar $k_{on}$ values (only 3-fold difference between the lowest and highest $k_{on}$ values). In contrast $k_{off}$ values of mAbs 5A4 and 9H9 are ~2 orders of magnitude lower than that of 2D8 and 8E3. No binding to negative control antigen was observed with any of the mAbs.

TABLE 3

$K_d$, $k_{on}$ and $k_{off}$ values of chimeric D-galactan III specific mAbs

| mAb | $K_d$ | $k_{on}$ | $k_{off}$ |
|---|---|---|---|
| 2D8 | 1.12E−08 | 6.85E+04 | 7.66E−04 |
| 5A4 | 1.06E−10 | 9.19E+04 | 9.75E−06 |
| 9H9 | 3.40E−10 | 3.54E+04 | 1.20E−05 |
| 8E3 | 1.32E−08 | 6.29E+04 | 8.30E−04 |

Example 5: Surface Staining of Live Klebsiella Cells

Surface binding of one representative mAb (9H9-H7) was tested with flow cytometry on several clinical isolates of Klebsiella with different O-types (Table 4).

Overnight grown bacteria were diluted and grown to mid-log phase ($OD_{600}$=0.5), washed in PBS and used for surface staining. $2 \times 10^6$ bacteria were re-suspended in PBS containing 0.5% BSA+0.0.1% sodium azide, and stained with mAb 9H9-H7 in 40 µg/mL concentration for 30 minutes on ice. Samples were washed twice in PBS-buffer containing BSA and sodium azide, re-suspended in PBS containing 4 µg/mL AlexaFluor 488-conjugated goat anti-mouse IgG secondary antibody and incubated for 30 minutes on ice. After washing, samples were re-suspended in PBS containing 5 nM SYTO-62 dye and incubated for 10 minutes on ice before analysis on i-Cyt Eclipse flow cytometer.

The flow results (Table 4) corroborate that the investigated mAbs have specificity towards galactan-III (i.e. gtr positive strains) based on the results obtained with clinical gtr+ and gtr− strains.

TABLE 4

Surface staining by galactan-III specific mAbs of O1 and O2 strains with different gtr status. Values represent fluorescence intensity (FL-1)/1000

| | Strain | Sec. Ctrl | 2D8-A10 | 5A4-A7 | 9H9-H7 | 8E3-E5 |
|---|---|---|---|---|---|---|
| O2 gtr− | Kp20 | 4.2 | 4.2 | 4.2 | 4.4 | 4.1 |
| | Kp26 | 4.2 | 4.2 | 4.3 | 4.3 | 4.3 |
| O2 gtr+ | #79 | 4.3 | 281.1 | 230.1 | 157.8 | 288.9 |
| | Kp19 | 4.3 | 80.4 | 82.5 | 60.4 | 71.2 |

Furthermore, binding to a collection of ST258 strains was also determined by flow cytometry as described above (Table 5). 8/11 of the investigated strains were stained strongly by all four mAbs, one strain was proven to be rough and the two remaining strains showed a non-typeable LPS structure (data not shown). None of these strains reacted to a galactan-II specific mAb (see above).

TABLE 5

Surface staining by galactan-III specific mAbs of ST258 isolates. Values represent fluorescent intensity (FL-1).

| Strain | Sec. ctrl | 2D8-A10 | 5A4-A7 | 9H9-H7 | 8E3-E5 |
|---|---|---|---|---|---|
| Kp30 | 171 | 32066 | 40815 | 36796 | 41652 |
| Kp31 | 172 | 8720 | 10647 | 10797 | 16701 |
| Kp32 | 202 | 4040 | 4077 | 4739 | 5940 |
| Kp150 | 207 | 1616 | 2945 | 2249 | 2989 |
| Kp151 | 198 | 29495 | 26435 | 28560 | 37665 |
| Kp157 | 192 | 8344 | 9659 | 8849 | 10334 |
| Kp159 | 210 | 202 | 207 | 202 | 201 |
| Kp160 | 222 | 210 | 219 | 216 | 214 |
| Kp161 | 213 | 2517 | 7644 | 5352 | 4304 |
| Kp162 | 214 | 4366 | 8962 | 5891 | 4681 |

Example 6: Comparison of Functional Efficacy of the Different Galactan-III Specific mAbs Chimeric mAbs were generated in which mouse variable regions (VH and VL, for the heavy and light chains, respectively) were genetically fused to human IgG1 and kappa constant regions. Following testing in different functional assays in vitro and in vivo (see below), the best chimeric mAbs were subjected to humanization. Humanization was achieved by grafting the CDR sequences of both heavy and light chains from murine framework regions into corresponding (in silico predicted) human frameworks. Consequently, in these humanized mAbs the sole mouse-derived sequences are the CDR regions, the rest of the mAbs comprise of human sequences.

Furthermore, humanized light chains were paired to different humanized heavy chains (light chain shuffling, see FIG. 9). Interestingly mAbs comprising of 5A4 derived humanized light chains appeared to exhibit significantly higher efficacy, implying that these particular light chain CDR regions may contribute to the superior efficacy of some mAbs. Binding of the humanized mAbs was confirmed by surface staining of specific bacteria as assessed by flow cytometry (FIG. 9).

Example 7: Protective Efficacy of Gal-III Specific mAbs In Vivo

Groups of 5 mice were passively immunized intraperitoneally with chimeric (FIG. 10A) or humanized (FIG. 10B) galactan-III specific mAbs or isotype matched irrelevant mAb as control. 24 h later mice were sensitized to endotoxin by intraperitoneal administration of 20 mg of GalN and simultaneously challenged with a lethal dose of K. pneumoniae strain #79. Mortality was monitored daily.

All chimeric mAbs tested showed significant protection at doses of as low as 1 μg/mouse (FIG. 10A) corresponding to approx. 50 μg/kg dose. mAb 5A4 showed superior protective efficacy, which is in good correlation with its higher affinity (example 4) and in vitro LPS neutralization potency (example 8, below).

The most efficacious humanized mAbs with respect to endotoxin neutralization potential (see below in example 8) were tested in the same model. Since all of the humanized mAbs carried the 5A4-derived light chain CDR-s, protective efficacy was benchmarked against the chimeric mAb 5A4. As shown on FIG. 10B, the superior protective efficacy of most of the humanized mAbs was retained. Given that these humanized mabs contain different heavy chain CDR-s (but share the light chain CDR-s), it may be concluded that the light chain regions significantly contribute to the strong protective efficacy.

Example 8: In Vitro Neutralization of Endotoxin

Given the high serum susceptibility of K. pneumoniae O2 strains, we have proposed that endotoxin neutralization and not bactericidal activity may be the primary mode of action for protection described above (Example 7). In order to corroborate this experimentally endotoxin neutralization potency of galactan-III specific mAbs was investigated in vitro.

A commercial reporter cell line (HEK-Blue™ TLR4, Invivogen) was used to detect Toll like receptor 4 (TLR-4) signalling triggered by purified LPS according to the manufacturer's instructions. Thirty-five μl of mAb (diluted in HEK Blue™ medium) was mixed with 25 μl of freshly thawed purified LPS. O2 gtr+ LPS derived from strain PCM-27 (O2 gtr+:K27 Polish Collection of Microbes, Poland). Stock solutions were prepared at 0.4 ng/ml concentration in HEK Blue™ medium. Mixture was transferred into clear 96-well half-area plates and incubated at room temperature for 30 minutes. Fifty μl suspension of HEK-Blue™ cells was added (~50,000 cells/well). Plates were wrapped in aluminium foil and incubated overnight (16-18 hours) at 37° C. with 5% $CO_2$. On the following day optical density was measured at 630 nm and reporter protein level (secreted embryonic alkaline phosphatase—SEAP) over mock was calculated. Percent inhibition of SEAP induction relative to no antibody control was calculated and plotted at different mAb concentration. 50% inhibitory concentration (1050) was calculated with GraphPad Prism 5.0 using log (inhibitor) vs. response-variable slope nonlinear regression analysis. As positive control polymyxin B (PMB-Sulfate, FLUKA Cat. #81334) was used similar to the tested mAbs. As negative control, an irrelevant mAb was included.

Neutralization potential of humanized mAbs was compared to their parental (with respect to the heavy chain, since humanized light chains were shuffled) chimeric mAbs at 1 ug/ml mAb doses (FIG. 11). At this dose, chimeric mAb 5A4 showed superior neutralizing potency to the other chimeric mAbs, which is in good correlation with the affinities as measured by BLI (Example 4). Interestingly, some humanized derivatives of each heavy chain lineages showed a comparably good neutralization to chimeric 5A4, when paired with the 5A4 derived humanized light chain. This observation, again, suggests that the 5A4 light chain CDR sequences may confer an improved neutralization potency and hence the in vivo protection described above (Example 7).

In order to further support this finding, the best humanized mAbs of each lineage as well as their parental chimeric mAbs were titrated in the same in vitro neutralization assay. As depicted on FIG. 12., all mAbs carrying the 5A4 derived light chain CDR-s, exhibited a neutralization potency superior to that of polymixin B (a small molecule antibiotic with known endotoxin binding characteristics), whereas the remaining mAbs showed neutralization at higher doses, only.

REFERENCES (1) Hansen D S, Mestre F, Alberti S, et al. *Klebsiella pneumoniae* lipopolysaccharide O typing: revision of prototype strains and O-group distribution among clinical isolates from different sources and countries. J Clin Microbiol 1999 January; 37(1):56-62.

(2) Trautmann M, Ruhnke M, Rukavina T, et al. O-antigen seroepidemiology of *Klebsiella* clinical isolates and implications for immunoprophylaxis of *Klebsiella* infections. Clin Diagn Lab Immunol 1997 September; 4(5): 550-5.

(3) Clarke B R, Whitfield C. Molecular cloning of the rfb region of *Klebsiella pneumoniae* serotype O1:K20: the rfb gene cluster is responsible for synthesis of the D-galactan I O polysaccharide. J Bacteriol 1992 July; 174(14):4614-21.

(4) Hsieh P F, Wu M C, Yang F L, et al. D-galactan II is an immunodominant antigen in O1 lipopolysaccharide and affects virulence in *Klebsiella pneumoniae*: implication in vaccine design. Front Microbiol 2014; 5:608.

(5) R. F. Kelly, M. B. Perry, L. L. MacLean, C. Whitfield. Structures of the O-antigens of *Klebsiella* serotypes O2 (2a,2e), O2 (2a, 2e, 2h), and O2 (2a, 2f, 2g) members of a family of related D-galactan O-antigens in *Klebsiella* spp. Journal of Endotoxin Research 1995; 2:131-40.

(6) Allison G E, Verma N K. Serotype-converting bacteriophages and O-antigen modification in Shigella flexneri. Trends Microbiol 2000 January; 8(1):17-23.

The invention claimed is:

1. An isolated antibody comprising an antigen-binding site that specifically recognizes a galactan-III epitope of the lipopolysaccharide (LPS) O-antigen structure of *Klebsiella pneumoniae*, which epitope is incorporated in galactan-III repeating units, wherein
   each galactan-III repeating unit is a branched galactose homopolymer of Formula (I)

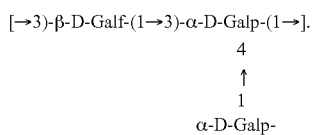

Formula (I)

which antigen-binding site is of an antibody heavy chain variable region (VH), which comprises a combination of VH-CDR sequences designated as CDR1 to CDR3, and an antibody light chain variable region (VL), which comprises a combination of VL-CDR sequences designated as CDR4 to CDR6,
wherein the antibody is selected from the group consisting of:
   i) is an antibody which comprises
      a) a CDR1 consisting of the amino acid sequence of SEQ ID NO:7;
      b) a CDR2 consisting of the amino acid sequence of SEQ ID NO:8;
      c) a CDR3 consisting of the amino acid sequence of SEQ ID NO:9;
      d) a CDR4 consisting of the amino acid sequence of SEQ ID NO:19;
      e) a CDR5 consisting of the amino acid sequence of SEQ ID NO:20; and
      f) a CDR6 consisting of the amino acid sequence of SEQ ID NO:18;
   ii) is an antibody which comprises
      a) a CDR1 consisting of the amino acid sequence of SEQ ID NO:1;
      b) a CDR2 consisting of the amino acid sequence of SEQ ID NO:2;
      c) a CDR3 consisting of the amino acid sequence of SEQ ID NO:3;
      d) a CDR4 consisting of the amino acid sequence of SEQ ID NO:13;
      e) a CDR5 consisting of the amino acid sequence of SEQ ID NO:14; and
      f) a CDR6 consisting of the amino acid sequence of SEQ ID NO:15;
   iii) is an antibody which comprises
      a) a CDR1 consisting of the amino acid sequence of SEQ ID NO:4;
      b) a CDR2 consisting of the amino acid sequence of SEQ ID NO:5;
      c) a CDR3 consisting of the amino acid sequence of SEQ ID NO:6;
      d) a CDR4 consisting of the amino acid sequence of SEQ ID NO:16;
      e) a CDR5 consisting of the amino acid sequence of SEQ ID NO:17; and
      f) a CDR6 consisting of the amino acid sequence of SEQ ID NO:18;

iv) is an antibody which comprises
  a) a CDR1 consisting of the amino acid sequence of SEQ ID NO:10;
  b) a CDR2 consisting of the amino acid sequence of SEQ ID NO:11;
  c) a CDR3 consisting of the amino acid sequence of SEQ ID NO:12;
  d) a CDR4 consisting of the amino acid sequence of SEQ ID NO:19;
  e) a CDR5 consisting of the amino acid sequence of SEQ ID NO:17; and
  f) a CDR6 consisting of the amino acid sequence of SEQ ID NO:18;
v) is an antibody which comprises
  a) a CDR1 consisting of the amino acid sequence of SEQ ID NO:4;
  b) a CDR2 consisting of the amino acid sequence of SEQ ID NO:5;
  c) a CDR3 consisting of the amino acid sequence of SEQ ID NO:6;
  d) a CDR4 consisting of the amino acid sequence of SEQ ID NO:19;
  e) a CDR5 consisting of the amino acid sequence of SEQ ID NO:20; and
  f) a CDR6 consisting of the amino acid sequence of SEQ ID NO:18; and
vi) is an antibody which comprises
  a) a CDR1 consisting of the amino acid sequence of SEQ ID NO:10;
  b) a CDR2 consisting of the amino acid sequence of SEQ ID NO:11;
  c) a CDR3 consisting of the amino acid sequence of SEQ ID NO:12;
  d) a CDR4 consisting of the amino acid sequence of SEQ ID NO:19;
  e) a CDR5 consisting of the amino acid sequence of SEQ ID NO:20; and
  f) a CDR6 consisting of the amino acid sequence of SEQ ID NO:18.

2. The antibody of claim 1, wherein the galactan-III epitope is of multi-drug resistant (MDR) *Klebsiella pneumoniae*.

3. The antibody of claim 1, which neutralizes endotoxin of *Klebsiella pneumoniae* strains expressing the galactan-III epitope and has an affinity to bind the galactan-III epitope with a Kd of less than $10^{-7}$M.

4. A pharmaceutical preparation comprising the antibody of claim 1, comprising a parenteral or mucosal formulation, which contains a pharmaceutically acceptable carrier or excipient.

5. A diagnostic preparation or a kit comprising
  a) the antibody of claim 1;
  b) a further diagnostic reagent;
  c) and optionally a solid phase to immobilize the antibody or the diagnostic reagent or both;
  wherein the diagnostic preparation is a composition.

6. The diagnostic preparation of claim 5, wherein the further diagnostic reagent is a diagnostic label or a reagent specifically reacting with the antibody and/or the reaction product of the antibody binding to the galactan-III epitope of the LPS O-antigen structure.

7. The antibody of claim 1, which is any of the following:
  a) an antibody comprising the VH sequence of SEQ ID NO:21, and the VL sequence of SEQ ID NO:22; or
  b) an antibody comprising the VH sequence of SEQ ID NO:23, and the VL sequence of SEQ ID NO:24; or
  c) an antibody comprising the VH sequence of SEQ ID NO:25, and the VL sequence of SEQ ID NO:26; or
  d) an antibody comprising the VH sequence of SEQ ID NO:27, and the VL sequence of SEQ ID NO:28; or
  e) an antibody comprising the VH sequence of SEQ ID NO:29, and the VL sequence of SEQ ID NO:30; or
  f) an antibody comprising the VH sequence of SEQ ID NO:31, and the VL sequence of SEQ ID NO:32; or
  g) an antibody comprising the VH sequence of SEQ ID NO:33, and the VL sequence of SEQ ID NO:34; or
  h) an antibody comprising the VH sequence of SEQ ID NO:35, and the VL sequence of SEQ ID NO:36; or
  i) an antibody comprising the VH sequence of SEQ ID NO:37, and the VL sequence of SEQ ID NO:38,
  or which is a human, humanized, chimeric, murine, or affinity matured variant of any of the foregoing comprising said antigen-binding site.

8. The diagnostic preparation of claim 5, wherein the composition or kit further comprises a solid phase to immobilize the antibody or the diagnostic reagent or both.

9. The antibody of claim 2, wherein the galactan-III epitope is the galactan-III epitope of the MDR clone ST258.

10. A method of protecting against *Klebsiella pneumoniae* comprising administering an effective amount of the antibody of claim 1 to a mammalian subject at risk of *Klebsiella pneumoniae* infection or *Klebsiella pneumoniae* colonization, or to a patient suffering from *Klebsiella pneumoniae* infection.

11. A method of diagnosing a *Klebsiella pneumoniae* infection or colonization by a *Klebsiella pneumoniae* strain in a mammalian subject, the method comprising:
  (a) providing a biological sample of the subject and providing the antibody according to claim 1, and
  (b) detecting the specific binding of the antibody to the galactan-III epitope of the LPS O-antigen structure of the *Klebsiella pneumoniae* strain in the biological sample of the subject, thereby diagnosing the *Klebsiella pneumoniae* infection or the *Klebsiella pneumoniae* colonization.

12. The method of claim 10, wherein the biological sample is a body fluid or a tissue sample.

13. The method of claim 12, wherein the body fluid or the tissue sample is selected from the group consisting of a blood sample, stool sample, skin sample, urine sample, cerebrospinal sample, and respiratory tract specimen.

14. The method of claim 13, wherein the respiratory tract specimen is an endotracheal aspirate, pleural fluid, lung tap, nasal swab, or sputum.

* * * * *

SEQUENCE LISTING

```
<160> NUMBER OF SEQ ID NOS: 40

<210> SEQ ID NO 1
<211> LENGTH: 9
<212> TYPE: PRT
<213> ORGANISM: Artificial Sequence
<220> FEATURE:
<223> OTHER INFORMATION: CDR Sequence

<400> SEQUENCE: 1

Phe Thr Phe Ser Asn Tyr Trp Ile Asn
1               5

<210> SEQ ID NO 2
<211> LENGTH: 19
<212> TYPE: PRT
<213> ORGANISM: Artificial Sequence
<220> FEATURE:
<223> OTHER INFORMATION: CDR Sequence

<400> SEQUENCE: 2

Glu Ile Arg Leu Lys Ser Asn Asn Tyr Ala Thr Tyr Tyr Val Glu Ser
1               5                   10                  15

Val Lys Gly

<210> SEQ ID NO 3
<211> LENGTH: 9
<212> TYPE: PRT
<213> ORGANISM: Artificial Sequence
<220> FEATURE:
<223> OTHER INFORMATION: CDR Sequence

<400> SEQUENCE: 3

Thr Lys Glu Tyr Gly Gly Phe Ala Asn
1               5

<210> SEQ ID NO 4
<211> LENGTH: 9
<212> TYPE: PRT
<213> ORGANISM: Artificial Sequence
<220> FEATURE:
<223> OTHER INFORMATION: CDR Sequence

<400> SEQUENCE: 4
```

```
Leu Ala Phe Ser Asn Tyr Trp Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: CDR Sequence

<400> SEQUENCE: 5

Glu Ile Arg Leu Lys Ser Asn Ser Tyr Ser Thr His Tyr Ala Glu Ser
1               5                   10                  15

Val Lys Gly

<210> SEQ ID NO 6
<211> LENGTH: 9
<212> TYPE: PRT
<213> ORGANISM: Artificial Sequence
<220> FEATURE:
<223> OTHER INFORMATION: CDR Sequence

<400> SEQUENCE: 6

Thr Pro Glu Phe Gly Gly Phe Pro Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: CDR Sequence

<400> SEQUENCE: 7

Phe Thr Phe Ser Asp Tyr Trp Met Asn
1               5

<210> SEQ ID NO 8
<211> LENGTH: 19
<212> TYPE: PRT
<213> ORGANISM: Artificial Sequence
<220> FEATURE:
<223> OTHER INFORMATION: CDR Sequence

<400> SEQUENCE: 8

Glu Ile Arg Leu Lys Ser Asn Asn Tyr Ala Thr Tyr Tyr Ala Glu Ser
1               5                   10                  15

Val Lys Gly

<210> SEQ ID NO 9
<211> LENGTH: 9
<212> TYPE: PRT
<213> ORGANISM: Artificial Sequence
<220> FEATURE:
<223> OTHER INFORMATION: CDR Sequence

<400> SEQUENCE: 9

Leu Pro Glu Phe Gly Gly Phe Phe Tyr
1               5

<210> SEQ ID NO 10
<211> LENGTH: 9
<212> TYPE: PRT
<213> ORGANISM: Artificial Sequence
<220> FEATURE:
```

```
<223> OTHER INFORMATION: CDR Sequence

<400> SEQUENCE: 10

Phe Thr Phe Ser Asn Tyr Trp Met Asn
1               5

<210> SEQ ID NO 11
<211> LENGTH: 19
<212> TYPE: PRT
<213> ORGANISM: Artificial Sequence
<220> FEATURE:
<223> OTHER INFORMATION: CDR Sequence

<400> SEQUENCE: 11

Glu Ile Arg Leu Lys Ser Asn Asn Tyr Ala Thr His Tyr Ala Glu Ser
1               5                   10                  15

Val Lys Gly

<210> SEQ ID NO 12
<211> LENGTH: 9
<212> TYPE: PRT
<213> ORGANISM: Artificial Sequence
<220> FEATURE:
<223> OTHER INFORMATION: CDR Sequence

<400> SEQUENCE: 12

Thr Pro Glu Phe Gly Gly Phe Phe Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: CDR Sequence

<400> SEQUENCE: 13

Lys Ser Ser Gln Ser Leu Leu Tyr Ser Ser Asn Gln Lys Asn Cys Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: CDR Sequence

<400> SEQUENCE: 14

Trp Ala Ser Thr Arg Glu Ser
1               5

<210> SEQ ID NO 15
<211> LENGTH: 8
<212> TYPE: PRT
<213> ORGANISM: Artificial Sequence
<220> FEATURE:
<223> OTHER INFORMATION: CDR Sequence

<400> SEQUENCE: 15

His Gln Tyr Leu Ser Ser Tyr Thr
1               5

<210> SEQ ID NO 16
<211> LENGTH: 16
```

```
<212> TYPE: PRT
<213> ORGANISM: Artificial Sequence
<220> FEATURE:
<223> OTHER INFORMATION: CDR Sequence

<400> SEQUENCE: 16

Arg Ser Ser Gln Ser Leu Val His Ser Asp Gly Ser Thr Tyr Leu His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDR Sequence

<400> SEQUENCE: 17

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR Sequence

<400> SEQUENCE: 18

Ser Gln Ser Thr His Val Pro Trp Thr
1               5

<210> SEQ ID NO 19
<211> LENGTH: 16
<212> TYPE: PRT
<213> ORGANISM: Artificial Sequence
<220> FEATURE:
<223> OTHER INFORMATION: CDR Sequence

<400> SEQUENCE: 19

Arg Ser Ser Gln Ser Leu Val His Ser Asp Gly Asn Thr Tyr Leu His
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: CDR Sequence

<400> SEQUENCE: 20

Leu Val Ser Asn Arg Phe Ser
1               5

<210> SEQ ID NO 21
<211> LENGTH: 118
<212> TYPE: PRT
<213> ORGANISM: Artificial Sequence
<220> FEATURE:
<223> OTHER INFORMATION: VH Sequence

<400> SEQUENCE: 21

Glu Val Lys Leu Gln Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Ile Asn Trp Val Arg Gln Ser Pro Glu Lys Gly Leu Glu Trp Val
```

```
                35                  40                  45

Ala Glu Ile Arg Leu Lys Ser Asn Asn Tyr Ala Thr Tyr Tyr Val Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Lys Glu Tyr Gly Gly Phe Ala Asn Trp Gly Gln Gly Thr
            100                 105                 110

Thr Val Thr Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: VL Sequence

<400> SEQUENCE: 22

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Leu Leu Tyr Ser
            20                  25                  30

Ser Asn Gln Lys Asn Cys Leu Ala Trp Tyr Gln Arg Lys Pro Gly Gln
        35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

<210> SEQ ID NO 23
<211> LENGTH: 118
<212> TYPE: PRT
<213> ORGANISM: Artificial Sequence
<220> FEATURE:
<223> OTHER INFORMATION: VH Sequence

<400> SEQUENCE: 23

Glu Val Lys Leu Gln Glu Ser Gly Gly Gly Leu Val Gln Pro Gly Gly
1               5                   10                  15

Ser Met Lys Leu Ser Cys Val Ala Ser Gly Leu Ala Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Ser Tyr Ser Thr His Tyr Ala Glu
        50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Tyr Cys Thr Pro Glu Phe Gly Gly Phe Pro Tyr Trp Gly Gln Gly Thr
            100                 105                 110
```

Thr Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: VL Sequence

<400> SEQUENCE: 24

Asp Val Val Met Thr Gln Thr Pro Leu Ser Leu Pro Val Ser Leu Gly
1               5                   10                  15

Asp His Ala Ser Ile Ser Cys Arg Ser Ser Gln Ser Leu Val His Ser
            20                  25                  30

Asp Gly Ser Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 25
<211> LENGTH: 118
<212> TYPE: PRT
<213> ORGANISM: Artificial Sequence
<220> FEATURE:
<223> OTHER INFORMATION: VH Sequence

<400> SEQUENCE: 25

Glu Val Asn Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr Tyr Tyr Ala Glu
    50                  55                  60

Ser Val Lys Gly Arg Phe Thr Ile Ser Arg Asp Asp Ser Lys Arg Ser
65                  70                  75                  80

Val Tyr Leu Arg Val Asn Asn Leu Arg Val Glu Asp Thr Gly Ile Tyr
                85                  90                  95

Tyr Cys Leu Pro Glu Phe Gly Gly Phe Phe Tyr Trp Gly Gln Gly Thr
            100                 105                 110

Leu Val Thr Val Ser Ala
        115

<210> SEQ ID NO 26
<211> LENGTH: 112
<212> TYPE: PRT
<213> ORGANISM: Artificial Sequence
<220> FEATURE:
<223> OTHER INFORMATION: VL Sequence

<400> SEQUENCE: 26

Asp Val Leu Met Thr Gln Thr Pro Leu Ser Leu Pro Val Arg Leu Gly

```
                1               5                   10                  15
Asp Gln Ala Ser Ile Ser Cys Arg Ser Ser Gln Ser Leu Val His Ser
                20                  25                  30

Asp Gly Asn Thr Tyr Leu His Trp Tyr Leu Gln Arg Pro Gly Gln Ser
            35                  40                  45

Pro Lys Leu Leu Ile Asn Leu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110
```

<210> SEQ ID NO 27
<211> LENGTH: 118
<212> TYPE: PRT
<213> ORGANISM: Artificial Sequence
<220> FEATURE:
<223> OTHER INFORMATION: VH Sequence

<400> SEQUENCE: 27

```
Glu Val Lys Leu Gln Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Glu Phe Gly Gly Phe Phe Tyr Trp Gly Gln Gly Thr
                100                 105                 110

Thr Val Thr Val Ser Ser
        115
```

<210> SEQ ID NO 28
<211> LENGTH: 112
<212> TYPE: PRT
<213> ORGANISM: Artificial Sequence
<220> FEATURE:
<223> OTHER INFORMATION: VL Sequence

<400> SEQUENCE: 28

```
Asp Val Val Met Thr Gln Thr Pro Leu Ser Leu Pro Val Asn Leu Gly
1               5                   10                  15

Asp Gln Ala Ser Ile Ser Cys Arg Ser Ser Gln Ser Leu Val His Ser
                20                  25                  30

Asp Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

<210> SEQ ID NO 29
<211> LENGTH: 118
<212> TYPE: PRT
<213> ORGANISM: Artificial Sequence
<220> FEATURE:
<223> OTHER INFORMATION: VH Sequence

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr Tyr Tyr Ala Glu
50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Leu Pro Glu Phe Gly Gly Phe Phe Tyr Trp Gly Gln Gly Thr
            100                 105                 110

Leu Val Thr Val Ser Ser
        115

<210> SEQ ID NO 30
<211> LENGTH: 112
<212> TYPE: PRT
<213> ORGANISM: Artificial Sequence
<220> FEATURE:
<223> OTHER INFORMATION: VL Sequence

<400> SEQUENCE: 30

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Asn Leu Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 31
<211> LENGTH: 118
<212> TYPE: PRT
<213> ORGANISM: Artificial Sequence
<220> FEATURE:
<223> OTHER INFORMATION: VH Sequence

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr Tyr Tyr Ala Glu
    50                  55                  60

Ser Val Lys Gly Arg Phe Thr Ile Ser Arg Asp Asp Ser Lys Arg Thr
65                  70                  75                  80

Val Tyr Leu Gln Met Asn Ser Leu Arg Ala Glu Asp Thr Ala Val Tyr
                85                  90                  95

Tyr Cys Leu Pro Glu Phe Gly Gly Phe Phe Tyr Trp Gly Gln Gly Thr
            100                 105                 110

Leu Val Thr Val Ser Ser
        115

<210> SEQ ID NO 32
<211> LENGTH: 112
<212> TYPE: PRT
<213> ORGANISM: Artificial Sequence
<220> FEATURE:
<223> OTHER INFORMATION: VL Sequence

<400> SEQUENCE: 32

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Asn Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 33
<211> LENGTH: 118
<212> TYPE: PRT
<213> ORGANISM: Artificial Sequence
<220> FEATURE:
<223> OTHER INFORMATION: VH Sequence

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Ala Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Ser Tyr Ser Thr His Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Pro Glu Phe Gly Gly Phe Pro Tyr Trp Gly Gln Gly Thr
            100                 105                 110

Leu Val Thr Val Ser Ser
            115

<210> SEQ ID NO 34
<211> LENGTH: 112
<212> TYPE: PRT
<213> ORGANISM: Artificial Sequence
<220> FEATURE:
<223> OTHER INFORMATION: VL Sequence

<400> SEQUENCE: 34

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Asn Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 35
<211> LENGTH: 118
<212> TYPE: PRT
<213> ORGANISM: Artificial Sequence
<220> FEATURE:
<223> OTHER INFORMATION: VH Sequence

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Ala Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Ser Tyr Ser Thr His Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Pro Glu Phe Gly Gly Phe Pro Tyr Trp Gly Gln Gly Thr
            100                 105                 110

Leu Val Thr Val Ser Ser
            115

<210> SEQ ID NO 36

<211> LENGTH: 112
<212> TYPE: PRT
<213> ORGANISM: Artificial Sequence
<220> FEATURE:
<223> OTHER INFORMATION: VL Sequence

<400> SEQUENCE: 36

```
Asp Val Gln Met Thr Gln Ser Pro Ser Ser Leu Ser Ala Ser Val Gly
1               5                   10                  15
Asp Arg Val Thr Ile Thr Cys Arg Ser Ser Gln Ser Leu Val His Ser
            20                  25                  30
Asp Gly Asn Thr Tyr Leu His Trp Tyr Gln Gln Lys Pro Gly Lys Ser
        35                  40                  45
Pro Lys Leu Leu Ile Asn Leu Val Ser Asn Arg Phe Ser Gly Val Pro
    50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Ser Gln Ser
                85                  90                  95
Thr His Val Pro Trp Thr Phe Gly Gly Gly Thr Lys Val Glu Ile Lys
            100                 105                 110
```

<210> SEQ ID NO 37
<211> LENGTH: 118
<212> TYPE: PRT
<213> ORGANISM: Artificial Sequence
<220> FEATURE:
<223> OTHER INFORMATION: VH Sequence

<400> SEQUENCE: 37

```
Glu Val Gln Leu Leu Glu Ser Gly Gly Gly Leu Val Gln Pro Gly Gly
1               5                   10                  15
Ser Leu Arg Leu Ser Cys Ala Val Ser Gly Phe Thr Phe Ser Asn Tyr
            20                  25                  30
Trp Met Asn Trp Val Arg Gln Ala Pro Gly Lys Gly Leu Glu Trp Val
        35                  40                  45
Ala Glu Ile Arg Leu Lys Ser Asn Asn Tyr Ala Thr His Tyr Ala Glu
    50                  55                  60
Ser Val Lys Gly Arg Phe Thr Ile Ser Arg Asp Asp Ser Lys Ser Thr
65                  70                  75                  80
Val Tyr Leu Gln Met Asn Ser Leu Arg Ala Glu Asp Thr Ala Val Tyr
                85                  90                  95
Tyr Cys Thr Pro Glu Phe Gly Gly Phe Phe Tyr Trp Gly Gln Gly Thr
            100                 105                 110
Leu Val Thr Val Ser Ser
        115
```

<210> SEQ ID NO 38
<211> LENGTH: 112
<212> TYPE: PRT
<213> ORGANISM: Artificial Sequence
<220> FEATURE:
<223> OTHER INFORMATION: VL Sequence

<400> SEQUENCE: 38

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
```

```
Asp Gly Asn Thr Tyr Leu His Trp Tyr Leu Gln Lys Pro Gly Gln Ser
             35                  40                  45

Pro Gln Leu Leu Ile Asn Leu Val Ser Asn Arg Phe Ser Gly Val Pro
         50                  55                  60

Asp Arg Phe Ser Gly Ser Gly Ser Gly Thr Asp Phe Thr Leu Lys Ile
 65              70                  75                  80

Ser Arg Val Glu Ala Glu Asp Val Gly Val Tyr Tyr Cys Ser Gln Ser
                 85                  90                  95

Thr His Val Pro Trp Thr Phe Gly Gly Gly Thr Lys Val Glu Ile Lys
                100                 105                 110

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
tgttgtggag taaaggactg ggcg                                        24

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
accgcttcga gctgaagaat gag                                         23
```